US010928350B2

(12) United States Patent
Lee et al.

(10) Patent No.: US 10,928,350 B2
(45) Date of Patent: Feb. 23, 2021

(54) ELECTROCHEMICAL METHOD AND APPARATUS

(71) Applicant: Oxford University Innovation Limited, Oxford (GB)

(72) Inventors: Patricia Tung Lee, Oxford (GB); Denise Lowinsohn, Oxford (GB); Richard Guy Compton, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 359 days.

(21) Appl. No.: 15/127,315

(22) PCT Filed: Mar. 20, 2015

(86) PCT No.: PCT/GB2015/050823
§ 371 (c)(1),
(2) Date: Sep. 19, 2016

(87) PCT Pub. No.: WO2015/140568
PCT Pub. Date: Sep. 24, 2015

(65) Prior Publication Data
US 2017/0138884 A1 May 18, 2017

(30) Foreign Application Priority Data

Mar. 21, 2014 (GB) ..................................... 1405130

(51) Int. Cl.
G01N 27/30 (2006.01)
G01N 27/48 (2006.01)
G01N 33/68 (2006.01)

(52) U.S. Cl.
CPC .......... G01N 27/308 (2013.01); G01N 27/48 (2013.01); G01N 33/6815 (2013.01)

(58) Field of Classification Search
CPC ... G01N 27/308; G01N 27/48; G01N 33/6815
See application file for complete search history.

(56) References Cited

PUBLICATIONS

P. T. Lee, K. R. Ward, K. Tschulik, G. Chapman, and R. G. Compton, "Electrochemical Detection of Glutathione Using a Poly(caffeic acid) Nanocarbon Composite Modified Electrode", Electroanalysis 2014, 26, 366-373.*
Hamid Salehzadeh, Banafsheh Mokhtari, Davood Nematollahi, "Selective electrochemical determination of homocysteine in the presence of cysteine and glutathione", Electrochimica Acta 123 (2014) 353-361 (Year: 2014).*

(Continued)

*Primary Examiner* — Mayla Gonzalez Ramos
(74) *Attorney, Agent, or Firm* — Lathrop GPM LLP; James H. Velema, Esq.

(57) ABSTRACT

Herein is disclosed a method for detecting a material comprising a thiol group (e.g. homocysteine, cysteine, glutathione) in a sample, the method comprising: •providing an electrode comprising a carbon material; •contacting said electrode with said sample in the presence of catechol or more generally a precursor of ortho-quinone; •performing cyclic or square wave voltammetry to convert catechol to ortho-quinone and wherein said ortho-quinone reacts with the material comprising a thiol group to form an electrochemical reaction product.

16 Claims, 22 Drawing Sheets

(56) References Cited

PUBLICATIONS

Mojmir Baron, Jiri Sochor, "Estimation of Thiol Compounds Cysteine and Homocysteine in Sources of Protein by Means of Electrochemical Techniques", Int. J. Electrochem. Sci., 8 (2013) 11072-11086 (Year: 2013).*

Takayo Inoue and Jon R. Kirchhoff, "Electrochemical Detection of Thiols with a Coenzyme Pyrroloquinoline Quinone Modified Electrode", Anal. Chem. 2000, 72, 5755-5760 (Year: 2000).*

Pacsial-Ong et al. (2006) "Electrochemical detection of glutathione using redox indicators," Anal. Chem. 78 (21):7577-7581.

Raoof et al. (2009) "Fabrication of functionalized carbon nanotube modified glassy carbon electrode and its application for selective oxidation and voltammetric determination of cysteamine," Journal of Electroanalytical Chemistry. 633:187-192.

Search Report corresponding to Great Britain Patent Application No. 1405130.4, dated Oct. 16, 2014.

Hignett et al. (2001) "Electroanalytical exploitation of quinone—thiol interactions: application to the selective determination of cysteine," The Analyst. 126(3):353-357.

Lawrence (2001) "Electrochemical detection of thiols in biological media," Talanta. 53(5):1089-1094.

Lee et al. (Feb. 16, 2014) "Electrochemical Detection of Glutathione Using a Poly(caffeic acid) Nanocarbon Composite Modified Electrode," Electroanalysis. 26(2):366-373.

Lee et al. (Jul. 14, 2013) "Electrochemical Detection of NADH, Cysteine, or Glutathione Using a Caffeic Acid Modified Glassy Carbon Electrode," Electroanalysis. 25(7):1613-1620.

Lee et al. (Jun. 12, 2014) "The Use of Screen-Printed Electrodes in a Proof of Concept Electrochemical Estimation of Homocysteine and Glutathione in the Presence of Cysteine Using Catechol," Sensors. 14(6):10395-10411.

Liao et al. (2008) "Development of a method for total plasma thiols measurement using a disposable screen-printed carbon electrode coupled with a MnO2 reactor," Sensors and Actuators B: Chemical. 129(2):896-902.

Liu et al. (Oct. 1, 2012) "Differential Pulse Voltammetric Determination of L-Cysteine After Cyclic Voltammetry in Presence of Catechol with Glassy Carbon Electrode," Analytical Letters. 45(15):2246-2256.

Lowinsohn et al. (Apr. 14, 2014) "Towards Detection of Total Antioxidant Concentrations of Glutathione, Cysteine, Homocysteine and Ascorbic Acid Using a Nanocarbon Paste Electrode," Int. J. Electrochem. Sci. 3458-3472.

Nekrassova (2003) "Analytical determination of homocysteine: a review," Talanta. 60(6):1085-1095.

Raoof et al. (2010) "Catechol as an electrochemical indicator for voltammetric determination of N-acetyl-l-cysteine in aqueous media at the surface of carbon paste electrode," J. Appl. Electrochem. 40(7):1357-1363.

Salefizadeh et al. (Jan. 23, 2014) "Selective electrochemical determination of homocysteine in the presence of cysteine and glutathione," Electrochimica Acta. 123:353-361.

Seymour et al. (2002) "Electrochemical Detection of Glutathione: An Electrochemically Initiated Reaction Pathway," Analytical Letters. 35(8):1387-1399.

White et al. (2001) "Electrochemically initiated 1,4 additions: a versatile route to the determination of thiols," Analytica Chimica Acta. 447(1-2):1-10.

International Search Report with Written Opinion corresponding to International Patent Application No. PCT/GB2015/050823, dated Jun. 8, 2015.

* cited by examiner

ELECTROCHEMICAL METHOD AND APPARATUS

RELATED APPLICATIONS

This application is a 35 U.S.C. § 371 filing of International Application No. PCT/GB2015/050823, filed Mar. 20, 2015, which claims the benefit of priority of GB Patent Application No. 1405130.4, filed Mar. 21, 2014. The contents of the aforementioned applications are hereby incorporated by reference in their entireties for all purposes.

FIELD OF THE INVENTION

The present invention relates to an electrochemical method and apparatus suitable for carrying out said method for use in detecting and measuring the concentration of an antioxidant or antioxidants in a sample. The antioxidant(s) are typically thiol containing compounds. In particular, the present invention relates to a method, and apparatus suitable for carrying out said method, for use in the selective detection of one or more thiol compounds, for example the selective detection of one or more of glutathione, cysteine and homocysteine.

BACKGROUND OF THE INVENTION

Free radicals are reactive molecules arising physiologically during cellular aerobic metabolism. Their possible harmful effects for human health have raised increasing concern in recent years. They react rapidly with other compounds sometimes causing chain reactions. The resulting biochemical alterations are implicated in a growing list of human diseases, such as cardiovascular diseases, ageing, Parkinson's disease, Alzheimer's disease, diabetes and cancer.

Antioxidants are compounds that inhibit or delay the oxidation process by blocking the initiation or propagation of oxidizing chain reactions. Physiologically, the most relevant antioxidants include tocopherol (vitamin E), retinol (vitamin A), ascorbic acid (vitamin C), glutathione, cysteine and uric acid. Most studies in the literature for the electrochemical detection of antioxidants are focused on the food industry whereas in the biological area only a relatively few articles can be found. Although the presence of antioxidants may be beneficial, elevated levels can also be harmful.

Glutathione is the most prevalent cellular thiol and the most abundant low-molecular-weight peptide present in cells. Glutathione acts as an antioxidant, participating in detoxification for xenobiotics and metabolism of numerous cellular compounds. Homocysteine is an endogenous sulfhydryl amino acid, which is generated by the demethylation of methionine and the level in plasma or serum and is a sensitive indicator of vitamin $B_{12}$ and folate deficiencies. Cysteine is a sulfur containing amino acid and known to play an important role in various biochemical processes. As an antioxidant, ascorbic acid scavenges free radicals in the body and protects tissues from oxidative stress. Ascorbic acid also promotes the adsorption of iron, while preventing its oxidation.

Homocysteine, (HCys) is a thiol containing non-protein amino acid that partakes in biological functions that maintain metabolism. It was first hypothesized in the 1960s that increased levels of homocysteine may lead to implications in connection with leukemia, Alzheimer's disease, cancer and cardiovascular diseases such as atherosclerosis, arterial disease, and atherothrombotic vascular disease. Though a typical range of homocysteine in healthy blood plasma is 5-15 µM; studies have shown that elevated levels of homocysteine, ≥15 µM, can lead to any of the three classifications of hyperhomocystienemia which is a high risk factor for the diseases mentioned above. The three classifications of hyperhomocyteinemia are mild (15-30 µM), intermediate (30-100 µM), and severe (≥100 µM). Another example of a thiol-containing non-protein amino acid, which is also an antioxidant, is cysteine. Cystinosis is a disorder that can occur when cysteine concentrations in the plasma are above 30 µM.

Some methods of antioxidant detection, such as homocysteine detection, include spectroscopy (e.g. mass spectroscopy), chromatography coupled with spectroscopy, fluorescence, immunoassay, and electrochemistry. However, the use of analytical instrumentations has its drawbacks with it being expensive, time consuming, and requiring technical training and handling. In addition, these approaches require the use of a separation technique and sample pretreatment. The use of electroanalytical methods in the form of dedicated sensors has advantages over the detection methodologies mentioned above since measurements can be fast, easy and performed without any separation or purification of the sample. However, a problem associated with direct electrochemical detection is the poor voltammetric responses on conventional bare electrode surfaces due to the large oxidation over potential of materials (e.g. antioxidants) to be detected, for example homocysteine (ca. +0.40 V vs. SCE). Developing a quick, cost-effective and easy monitoring and/or detecting system of antioxidant levels, for example antioxidants comprising a thiol group such as homocysteine and/or cysteine, and/or glutathione in biological samples would be advantageous for early disease detection or research-based instrumentation.

As such, and given that existing electrochemistry techniques in the form of sensors are often coupled with separation techniques, it would be beneficial to provide a method or methods which provide selective electrochemical detection and, optionally, the simultaneous electrochemical detection, of an antioxidant or antioxidants, such as one or more compounds each possessing one or more thiol groups, preferably without the use of separation techniques and/or sample pretreatment.

The present invention seeks to address at least some of the issues raised above. In particular there is a need for alternative and preferably improved methods for detecting and determining the concentration of antioxidant(s), including thiol containing antioxidant(s), in samples.

SUMMARY OF THE INVENTION

In accordance with the present invention and in a first aspect there is provided a method of detecting a material comprising a thiol group in a sample, the method comprising:
providing an electrode comprising a carbon material;
contacting said electrode with said sample in the presence of catechol;
carrying out an electrochemical procedure to convert catechol to ortho-quinone and wherein the ortho-quinone reacts with the material comprising a thiol group to form an electrochemical reaction product.

In a second aspect, there is provided an apparatus for detecting a material comprised in a sample wherein said material comprises a thiol group, said apparatus comprising an electrode comprising a carbon material and catechol, the apparatus adapted to:

contact the sample comprising the material comprising a thiol group;

carry out an electrochemical procedure to convert the catechol to ortho-quinone and wherein the ortho-quinone reacts with the material comprising the thiol group to form an electrochemical product.

The electrochemical reaction product may be a 1,4-Michael addition reaction product of the ortho-quinone and the material comprising a thiol group and/or the electrochemical reaction product may comprise a disulfide and the regeneration of catechol.

The material comprising a thiol group may be an antioxidant. For example, the material comprising a thiol group may be selected from one or more of homocysteine, glutathione or cysteine. The method may comprise determining the concentration of homocysteine (HCys) in the presence of at least one of, or any combination of, glutathione (GSH), cysteine (Cys) and ascorbic acid (AA). The method may comprise determining the concentration of homocysteine in the absence of other antioxidants, for example in the absence of other thiols, for example in the absence of glutathione (GSH), cysteine (Cys) and ascorbic acid (AA).

The method may comprise determining the total concentration of homocysteine and cysteine, for example in the presence of ascorbic acid and glutathione. The homocysteine and cysteine may be detected simultaneously. The method may comprise detecting and determining the total concentration of glutathione, cysteine, homocysteine and ascorbic acid. The method may comprise detecting and determining the total concentration of homocysteine, glutathione and ascorbic acid. The method may comprise detecting and determining the total concentration of homocysteine and glutathione, for example the method may comprise detecting and determining the total concentration of glutathione and homocysteine, optionally in the presence of cysteine and/or ascorbic acid. The method may comprise detecting and determining the concentrations individually of homocysteine and of glutathione when they are both present in a sample, for example the method may comprise detecting and determining the concentration of glutathione and of homocysteine individually when they are present in a sample in the presence of cysteine and/or ascorbic acid. In relation to each of these embodiments the detection and/or determination of (total) concentration of antioxidant or antioxidants may be in relation to a sample, wherein said sample may or may not comprise one or more other antioxidants which may or may not comprise a thiol group.

The electrochemical procedure may comprise a voltammetry technique to determine the presence of the electrochemical reaction product or products. The voltammetry technique may comprise a cyclic voltammetry technique and/or a square wave voltammetry technique.

The electrode comprising a carbon material may be selected from: a glassy carbon electrode (GCE), a carbon nanotube modified glassy carbon electrode (CNT-GCE), a nanocarbon modified glassy carbon electrode (NC-GCE) or a nanocarbon paste electrode. The electrode may be pre-treated with catechol and/or the catechol may be in solution. The catechol may be absorbed or immobilized on the electrode comprising a carbon material. The catechol may be dissolved into the electrode. The material comprising a thiol group may react with the catechol on the electrode.

The electrode comprising a carbon material may form part of a three electrode system. The electrode comprising a carbon material may be the working electrode of a three electrode system. The three electrode system may comprise a reference electrode, counter electrode and the electrode comprising a carbon material may be a working electrode.

The concentration of the material comprising a thiol group may be in the range of up to about 300 µm, for example, about 0.01 µm to about 300 µm or to about 200 µm. The concentration of the catechol may typically be in the range of from about 50 to about 500 µM for example up to about 100 µM. The catechol may be unsubstituted (1,2-dihydroxybenzene) or the catechol may be substituted catechol. When the catechol is substituted, for example in one or more positions which may be with one or more substituents, the ortho-quinone formed in the electrochemical procedure (e.g. on electro-oxidation) may also be substituted, in one or more positions which may be with one or more substituents. When substituted with more than one substituent, the substituents may be the same chemical group or different chemical groups.

In the first and second aspects of the invention, the electrochemical procedure may, more generally, comprise converting a precursor of ortho-quinone to ortho-quinone. The precursor may be a precursor other than catechol or other than a substituted catechol. As such, in a third aspect there is provided a method of detecting a material comprising a thiol group in a sample, the method comprising:

providing an electrode comprising a carbon material;
contacting said electrode with said sample in the presence of a precursor of ortho-quinone;
carrying out an electrochemical procedure to convert the precursor of ortho-quinone to ortho-quinone and wherein the ortho-quinone reacts with the material comprising a thiol group to form an electrochemical reaction product.

Accordingly, in a fourth aspect, there is provided an apparatus for detecting a material comprised in a sample wherein said material comprises a thiol group, said apparatus comprising an electrode comprising a carbon material and a precursor of ortho-quinone, the apparatus adapted to:
contact the sample comprising the material comprising a thiol group;
carry out an electrochemical procedure to convert the precursor of ortho-quinone to ortho-quinone and wherein the ortho-quinone reacts with the material comprising the thiol group to form an electrochemical product.

In the third and fourth aspects, the pre-cursor may be other than catechol or other than a substituted catechol, for example it may be an aminophenol.

Typically, the electrochemical procedure comprises the electrochemical oxidation of the precursor to form ortho-quinone. For example, when the precursor is an aminophenol the electrochemical procedure comprises the formation of a quinone-imine which may (rapidly) hydrolyse to form the ortho-quinone.

Though certain embodiments of the present invention may tend to be described or discussed predominantly in relation to catechol, said references to catechol should not be construed as being limited to such embodiments. Said references are also appropriate in connection with the use of substituted catechol(s) and, more generally, precursors of ortho-quinone including those other than catechol.

The combined use of the electrode comprising a carbon material and catechol in accordance with the present invention provides a number of beneficial features. For example, the method and apparatus in accordance with the present invention provides for easy and straight-forward detection and determination of the concentration of a material or materials comprising a thiol group in a sample, optionally in the presence of additional materials. The method and apparatus provides for the selective detection and determination of concentration of one of said materials and the selective detection and determination of more than one of said materials. When more than one material is to be detected, said more than one material may comprise a material which does not comprise a thiol group. For example, thiols (e.g. antioxidants) may be detected and the concentration determined in the presence of one or more non thiols (e.g. antioxidants). The methods and apparatus in accordance with the present invention also provide advantageous levels of sensitivity.

Any feature in one aspect of the invention may be applied to any other aspect or aspects of the invention, in any appropriate combination. In particular, product, device, apparatus or article aspects may be applied to method aspects, and vice versa. Similarly, any feature in one embodiment of the invention may be applied to any other embodiment or embodiments of the invention, in any appropriate combination.

DETAILED DESCRIPTION OF THE INVENTION

Thiol

The material comprising a thiol group, which may simply be referred to herein as a thiol, may be any compound which possesses one or more thiol (SH) groups. The thiol may be an antioxidant. The thiol may be selected from one or more of the following compounds: homocysteine, cysteine, glutathione. The thiol or thiols may be present in a sample to be tested with other compounds. These other compounds may comprise other antioxidants. For example, the thiol or thiols may be present with ascorbic acid.

The method in accordance with the present invention may comprise the selective detection of a particular antioxidant, e.g. thiol compound, or may comprise the detection of a combination of antioxidants, e.g. thiol compounds, in a sample. For example, the method may comprise the selective detection of homocysteine when present with other compounds, for example when present with other thiols and/or non-thiols in a sample.

The method in accordance with the present invention may comprise the selective detection of homocysteine in the presence of one or any combination of glutathione, cysteine and ascorbic acid.

The method in accordance with the present invention may comprise the simultaneous detection of homocysteine and cysteine in the presence of glutathione and optionally, other antioxidants, for example ascorbic acid.

The method in accordance with the present invention may comprise the detection of the total concentration of glutathione, cysteine, homocysteine and ascorbic acid.

The method in accordance with the present invention may comprise the detection of the total concentration of glutathione, homocysteine and ascorbic acid.

The method in accordance with the present invention may comprise the detection, which may be simultaneous, of both homocysteine and glutathione in the same sample.

The method in accordance with the present invention may comprise the detection, which may or may not be simultaneous, of each of homocysteine and glutathione, so that their individual concentrations are provided, in a sample wherein the sample may also comprise cysteine and/or ascorbic acid.

The concentration of the material comprising a thiol group may be in the range of up to about 300 µm, for example, about 0.01 µm to about 300 µm or up to about 200 µm.

Electrode Comprising a Carbon Material

The electrode comprises a carbon material. Alternatively, the electrode may consist of, or consist essentially of, a carbon material.

Carbon electrodes have a relatively low cost compared to precious metal electrodes, chemical inertness and provide a wide potential range in aqueous solutions. The electrode comprising a carbon material may be selected from the following: glassy carbon electrode (GCE), carbon nanotube modified glassy carbon electrode (CNT-GCE), nanocarbon modified glassy carbon electrode (NC-GCE), nanocarbon paste electrode, carbon nanotube screen-printed carbon electrode (CNT-SPE).

Glassy Carbon Electrode (GCE)

The glassy carbon electrode is a standard glassy carbon electrode and its structure is comprised of interwoven ribbons of the graphite structure.

Carbon Nanotube Modified Glassy Carbon Electrode (CNT-GCE)

The CNT-GCE is typically prepared by modifying a standard glassy carbon electrode. The GCE may be polished, for example using a diamond spray. Following polishing, the GCE may be rinsed to remove the spray, for example using an alcohol such as ethanol followed by de-ionized water. Carbon nanotubes may be immobilized onto the surface of the GCE. A suitable procedure for immobilizing the carbon nanotubes may comprise the use of a drop casting method. Drop casting is a known technique and comprises the dropping of a suspension in a suitable carrier (e.g. ethanol) comprising CNT on to the surface of the GCE. The carrier is allowed to evaporate (typically at room temperature) leaving a layer of CNT at the electrode surface. To ensure a full suspension, the CNT and carrier may be sonicated, for example using a sonication bath) prior to drop casting. The surface area of the CNT-GCE may be obtained using cyclic voltammetry at scan rates ranging from about 25 to about 400 mVs$^{-1}$ in hexaammineruthenium (III) chloride and 0.1 M potassium chloride solution. The calculated average surface area for the CNT-GCE may range from about 0.21 to about 0.25 cm$^2$.

Nanocarbon Modified Glassy Carbon Electrode (NC-GCE)

Nanocarbon, sometimes referred to as 'carbon black', is essentially aggregates of carbon particles, often spherical which are of approximate size 10 nm, which make up a porous material. The size of the aggregate has an effect on the bulk material thus influencing the chemical and physical properties. Nanocarbon may be incorporated into the architecture of the electrode so that the surface of the electrode is directly modified. The NC-GCE is typically prepared by modifying a standard glassy carbon electrode. The GCE may be polished, for example using a diamond spray (for example in a descending order of diamond particle size, e.g. 3.0, 1.0, and 0.1 µm respectively). Following polishing, the GCE may be rinsed to remove the spray, for example using an alcohol such as ethanol followed by de-ionized water. Nanocarbon may be immobilized onto the surface of the GCE. A suitable procedure for immobilizing the nanocarbon may involve the use of a drop casting method. The drop casting method is a known technique and comprises the dropping of a suspension in a suitable carrier (e.g. ethanol) comprising NC on to the surface of the GCE. The carrier is allowed to evaporate (typically at room temperature) leaving a layer of NC at the electrode surface. To ensure a full suspension of the nanocarbon in solution (e.g. in ethanol), sonication may be used.

Nanocarbon Paste Electrode

The carbon paste may be prepared by (hand) pasting nanocarbon with mineral oil, typically in a ratio of about 55:45. The paste may be prepared by mixing the ingredients together, for example using a pestle and mortar. The nanocarbon catechol electrode may be prepared by combining a certain amount of solid catechol dissolved in a suitable solvent (e.g. acetone) and pasting together with nanocarbon and mineral oil. The solvent (e.g. acetone) is allowed to evaporate. Following evaporation, the catechol is distributed within the paste. Preferably, the pastes are kept in nitrogen atmosphere at room temperature to avoid oxidation.

Carbon Nanotube Screen-Printed Carbon Electrode (CNT-SPE)

Carbon nanotube screen-printed carbon electrodes may comprise multi-walled carbon nanotube screen printed electrodes, or graphite screen printed electrodes, (G-SPE). Suitable (disposable) screen printed electrodes may be acquired from DropSens (Spain) which typically possess a ceramic substrate comprising a multi-walled carbon nanotube or graphite working electrode, a carbon counter electrode and a silver reference electrode. The characterization using scanning electron microscopy (SEM) of these screen printed electrodes can be found on the DropSens website (www.dropsens.com/en/home.html).

Conversion of the Catechol to Ortho-Quinone and Reaction of the Ortho-Quinone with the Thiol to Form an Electrochemical Reaction Product Without wishing to be bound by theory, it is considered the reaction between ortho-quinone (which may be referred to herein as o-quinone) and thiols may proceed by two possible reaction pathways, one being an electrocatalytic reaction and the second a 1,4-Michael addition reaction. The electrocatalytic reaction involves the electrochemically oxidized ortho-quinone (from the catechol) undergoing a two electron, two proton process to reduce the thiol-containing species, RSH, into a disulfide, RSSR as shown in Scheme (1).

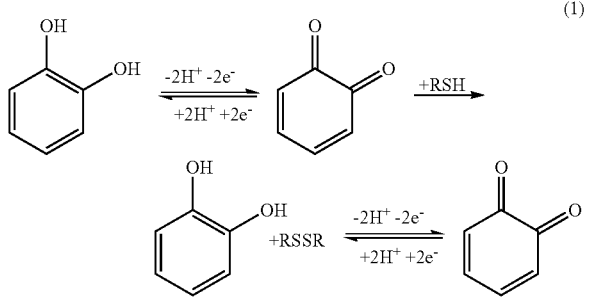

The reaction regenerates the starting catechol and continues catalytically until two electrons per RSSR formed due to the ortho-quinone being able to electrochemically re-oxidize itself from the electrons provided by the electrode. A cyclic voltammogram shows an increase in the forward (oxidation) peak and a decrease in the back (reduction) peak as the concentration of the thiol species increases. No new signal will appear in a voltammogram as the reaction is exclusively based on the quinone/hydroquinone redox reaction.

For the second type of reaction, the ortho-quinone may undergo a 1,4-Michael addition reaction as the thiol performs a nucleophillic attack on the oxidized ortho-quinone species resulting in a new electrochemical species. This type of reaction initially involves a two electron, two proton process to oxidize the catechol then an additional two electrons will be required for the nucleophillic attack to take place thus involving a net total of a four electron process as shown in Scheme (2).

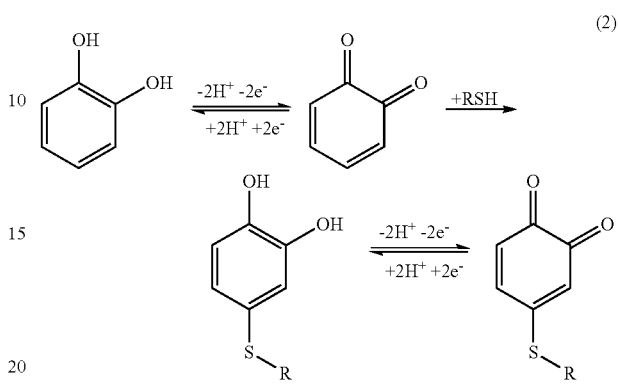

A voltammogram shows a forward peak increasing as the back peak decreases with increasing concentration of thiol species. In addition, the attack on the o-quinone species by a thiol may result in the introduction of a new peak away from the parent catechol peak potential due to the addition reaction.

The two possible reactions which can occur between an o-quinone group and a thiol containing molecule: 1,4-Michael addition and/or electrocatalytic reaction are also illustrated in FIG. 1. Oxidation of catechol is used to form o-quinone (leading to a current $I_{catechol}$). As a result of 1,4-Michael addition, the voltammogram (FIG. 1A) can show the introduction of a new signal (P1) and at maximum, with excess thiol, a four-electron process is seen for the catechol oxidation signal ($I_{catechol+thiol} \leq 2I_{catechol}$). During the electrocatalytic reaction, the catechol undergoes an electrochemical oxidation generating o-quinone which can mediate the oxidation of the thiol to produce disulfide. Subsequently, the catechol can be electrochemically re-oxidized. For this mechanism, the oxidation peak will increase and the reduction peak will decrease (FIG. 1B) as the concentration of the thiol species increases and no new signal will appear in the voltammograms as the reaction is exclusively based on the quinone/hydroquinone redox reaction. The catechol signal can show an effective number of electrons transferred in excess of two or even four for example in connection with fast reactions and large concentrations. The total concentration of glutathione, homocysteine, cysteine and ascorbic acid, for example, may be determined using the electrocatalytic reaction shown in Scheme (1) above and FIG. 1B.

Accordingly, the method in accordance with the present invention may comprise the formation of a product of a 1,4-Michael addition reaction of an ortho-quinone with an antioxidant. The method in accordance with the present invention may comprise the formation of a disulfide and the regeneration of catechol.

Homocysteine may be detected (selectively or simultaneously with another antioxidant, e.g. cysteine) using catechol via a 1,4-Michael addition reaction at an electrode comprising a carbon material in accordance with the present invention. For example, homocysteine and cysteine may be detected simultaneously, optionally selectively, in the presence of one or more other antioxidants, at a nanocarbon modified glassy carbon electrode (NC-GCE). Homocysteine may be detected selectively, optionally in the presence of another antioxidant, for example one or more of glutathione, cysteine and ascorbic acid, at an ordinary glassy carbon electrode or a carbon nanotube modified glassy carbon electrode (CNT-GCE).

The total concentrations (for example, the total biological concentrations) of the antioxidants glutathione, cysteine, homocysteine and ascorbic acid may be determined using an electrode comprising a carbon material, for example a nanocarbon paste electrode, via reaction between an electrochemically generated ortho-quinone and the four antioxidants. These four antioxidants may typically be found at high concentration in biological samples.

The total concentrations of the antioxidants glutathione, homocysteine and ascorbic acid may be determined using an electrode comprising a carbon material, for example a nanocarbon paste electrode, via reaction between an electrochemically generated ortho-quinone and the three oxidants.

The concentration of homocysteine and/or glutathione, when both homocysteine and glutathione are present in a sample, may be determined using an electrode comprising a carbon material, for example a carbon nanotube modified carbon electrode, via reaction between an electrochemically generated ortho-quinone and said antioxidants. Optionally, cysteine and/or ascorbic acid may be present in said sample. The individual concentrations of glutathione and homocysteine may be determined when both present in a given sample and optionally when cysteine and/or ascorbic acid are present.

Electrochemical Procedure

The electrochemical procedure (or electrochemical test) may comprise the use of a voltammetry technique. For example, the electrochemical procedure may comprise the use of cyclic voltammetry and/or square wave voltammetry. The cyclic voltammetry may be carried out at a scan rate of about 1 to about 1000 $mVs^{-1}$, for example 50 to about 800 $mVs^{-1}$, or to about 400 $mVs^{-1}$, or to about 300 $mVs^{-1}$. The square wave voltammetry may be carried out a frequency of from about 5 Hz to about 100 Hz, for example from about 25 Hz to about 50 Hz (particularly at the nanocarbon modified electrode) and/or a step potential of from about 0.5 to about 50 mV, for example, from about 8 mV or from about 10 mV (particularly at the carbon nanotube modified electrode) and/or an amplitude of about 1 mV to about 100 mV, for example, from about 50 mV (particularly at the nanocarbon modified electrode and the carbon nanotube modified electrode).

Voltammetry may be used to observe the electrochemical response of catechol in the presence of one or more antioxidants, e.g. one or more thiols. The voltammetric responses of the catechol in the absence and presence of one or more antioxidants (e.g. thiols) may be compared. When compared, the forward peak may be in a different position when comparing the samples with and without antioxidant. For example, in the presence of an antioxidant such as HCys, the voltammogram may show the current of the forward peak increased and the back peak decreased. A new product peak may also be present in the voltammetric response of the catechol in the presence of one or more antioxidants, for example due to the presence of the product resulting from the 1,4-Michael addition. This peak may be due to the reduction of the substituted catechol molecule as described in Scheme (2) above.

The electrochemical procedure may be carried out using a three electrode system. The electrode system may comprise a reference electrode, counter electrode and working electrode. The electrode comprising the carbon material for use in the present invention may be the working electrode. Saturated calomel electrode (SCE) is a suitable reference electrode and a suitable example of a counter electrode is a platinum mesh counter electrode. Typically, the electrochemical procedure may be carried out at about 20° C., for example at (20±2) ° C. in a Faraday cage. The pH of the electrochemical procedure may be monitored using known techniques, for example using a Microprocessor pH meter such as a pH213 Microprocessor pH meter obtainable from Hanna instruments. The pH meter may be calibrated using known techniques, for example using buffers at approximately pH 4, pH 7 and pH 10.

The electrochemical procedure or test may comprise obtaining a voltammogram to characterize the electrochemical behaviour of catechol in connection with a particular electrode. In this part of the procedure voltammograms may be taken at different scan rates. For example, to characterise the electrochemical behaviour of catechol the scan rates may range from about 25 $mVs^{-1}$ to about 400 $mVs^{-1}$. Characterisation may take place in phosphate buffered saline (PBS), at about pH7 and at about 20° C. The concentration of the catechol may typically be in the range of about 50 to about 100 μM. The $E_{1/2}$ of the catechol may be attributed to the two electron, two proton oxidation of the catechol to the corresponding ortho-quinone species and may typically be about +0.15 V (vs SCE).

As the concentration of the antioxidant increases the forward and new product peak may increase as the back peak decreases. The peak current of the new product peak may be plotted against the concentration of homocysteine. The existence of a linear trend indicates that homocysteine may be detected. More generally, and in connection with the various aspects of the present invention, the concentration of antioxidant (for example the concentration of HCys) may be determined by measuring the peak current.

The electrochemical procedure or test may comprise obtaining a voltammogram to detect the presence of one or more antioxidants (e.g. HCys) by observing the behaviour of catechol in the presence of the one or more antioxidants. For example cyclic voltammetry at scan rates ranging from about 10 $mVs^{-1}$ to about 1.5 $Vs^{-1}$ (e.g. 50 $mVs^{-1}$) may be carried out with a solution containing about 0 or 0.01 to about 5 mM of antioxidant. As the concentration of the antioxidant increases the forward and new product peak may increase as the back peak decreases. The peak current of the new product peak may be plotted against the concentration of antioxidant (e.g. homocysteine). The existence of a linear trend indicates that antioxidant (e.g. homocysteine) may be detected. More generally, and in connection with the various aspects of the present invention, the concentration of antioxidant (for example the concentration of HCys) may be determined by measuring the peak current.

The electrochemical procedure or test may comprise obtaining a square wave voltammogram to detect the presence of one or more antioxidants (e.g. HCys) by observing the behaviour of catechol in the presence of the one or more antioxidants. Typically, when comparing the voltammograms with and without the presence of one or more antioxidants (e.g. HCys) the catechol peak decreases and the new product peak increases with increasing antioxidant concentration. Hence, the peak current of the new product peak may be plotted against the concentration of antioxidant (e.g HCys). The existence of a linear trend indicates that homocysteine, for example, may be detected. More generally, and in connection with the various aspects of the present invention, the concentration of antioxidant (for example the concentration of HCys) may be determined by measuring the peak current. More specifically for a CNT-GCE electrode, the linear relationship may be given by I(μA)=0.2[HCys](μM). This relationship may be suitable for concentrations of antioxidant up to about 80 μM. For a GCE electrode, the linear relationship may be given by I(μA)=0.2 [HCys](μM). This relationship may be suitable for concentrations of antioxidant up to about 40 μM.

Advantageously, in order to improve the distinction between new product peaks, the scan rate may be increased. For example, in order to improve the selectivity for a particular antioxidant, such as homocysteine, and optimize the single signal attributable to that antioxidant the scan rate may be increased. For example, an optimum scan rate for use in connection with the use of a GCE using cyclic voltammetry may be from about $0.1\ Vs^{-1}$ to about $1.5\ Vs^{-1}$. For example, an optimum scan rate for use in connection with the use of a CNT-GCE may be about $0.5\ Vs^{-1}$, for a NC-GCE may be about $0.5\ Vs^{-1}$, and for a GCE may be about $1.5\ Vs^{-1}$. These scan rates are particularly advantageous when used for detecting homocysteine, particularly when in the presence of AA, Cys and GSH.

In connection with the use of a NC-GCE, the electrochemical procedure or test may comprise obtaining a voltammogram to characterize the electrochemical behaviour of catechol in connection with a NC-GCE. Voltammograms may be taken at different scan rates. For example, to characterise the electrochemical behaviour of catechol the scan rates may range from about 25 to about $400\ mVs^{-1}$ or to about $300\ mVs^{-1}$. Characterisation may take place in (PBS), at about pH7 and at about 20° C. The concentration of the catechol may typically be in the range of about 50 μM to about 500 μM, for example about 100 μM to about 300 μM. The cyclic voltammograms may split with increasing scan rate. The relationship between peak current with scan rate is linear or substantially linear. The catechol may physisorb onto the nanocarbon surface. In embodiments of the invention, the catechol may be present in solution or immobilized onto the surface of the electrode or a combination of both.

The electrochemical procedure or test may comprise obtaining a voltammogram to detect the presence of one or more antioxidants (e.g. HCys) by observing the behaviour of catechol in the presence of the one or more antioxidants in combination with an NC-GCE. For example cyclic voltammetry at a scan rate of about $50\ mVs^{-1}$ may be carried out with a solution containing about 0 or about 0.1 μM to about 100 μM of antioxidant, for example 0 or about 0.1 μM to about 100 μM for each of homocysteine and cysteine. The presence of homocysteine and cysteine may be detected simultaneously. The presence of a new peak potential may be present at about −0.16 V which may be due to the addition reaction of a thiol containing compound to the ortho-quinone moiety.

The electrochemical procedure or test may comprise obtaining a voltammogram to detect the presence solely of homocysteine by observing the behaviour of catechol with an NC-GCE. The relationship between a new peak potential (appearing at −0.16 V vs SCE), which may be due to the addition reaction of homocysteine to the ortho-quinone moiety may be given by the relationship I(μA)=+0.033 [HCys](μM) with homocysteine concentration. Cyclic voltammetry at a scan rate of about $50\ mVs^{-1}$ may be carried out with a solution containing about 0 or about 0.1 μM to about 100 μM of homocysteine.

Advantageously, to increase the sensitivity towards homocysteine detection, square wave voltammetry may be used. For example, there may be provided a linear response when the current of the homocysteine product peak is plotted with homocysteine concentration, I(μA)=+1.13 [HCys](μM). Using square wave voltammetry the sensitivity of homocysteine detection may be increased significantly, for example up to about thirty times when compared with cyclic voltammetry.

Typically, for NC-GCE, when comparing the cyclic voltammograms with and without the presence of one or more antioxidants (e.g. Cys) the catechol peak decreases and a new product peak increases with increasing antioxidant concentration. Hence, the peak current of the new product peak may be plotted against the concentration of antioxidant (e.g. Cys). The existence of a linear trend indicates that cysteine, for example, may be detected. More generally, and in connection with the various aspects of the present invention, the concentration of antioxidant (for example, the concentration of HCys) may be determined by measuring the peak current.

The NC-GCE may be used to determine the presence of cysteine using cyclic voltammetry, for example at a scan rate of 50 mVs-1. Typically a product peak may be present at about +0.3 V (vs SCE). Cyclic voltammetry may be applied to different concentrations of cysteine, for example up to about 0.1 mM. A linear relationship may be provided, for example I(μA)=3.96[Cys](nM).

Advantageously, square wave voltammetry may be applied to the electrochemical system comprising NC-GCE at varying antioxidant, e.g. cysteine, concentrations, with a view to detecting both homocysteine and cysteine in the same experiment. The square wave voltammogram may indicate the presence of a product peak at about +0.28 V (vs SCE) with increasing cysteine concentration. There may be a linear relationship when cysteine concentration is plotted with product peak current of cysteine such that I(μA)=9.71 [Cys](nM).

Cyclic voltammetry may be used to detect the presence of cysteine and homocysteine with the presence of other antioxidants such as GSH and/or AA for example using NC-GCE. This may be achieved for example by using a faster scan rate, for example of at least about $200\ mVs^{-1}$. In order to achieve simultaneous electrochemical detection of homocysteine and cysteine in the presence of ascorbic acid and glutathione square wave voltammetry may be used.

The total concentration of antioxidant, for example glutathione, cysteine, homocysteine and ascorbic acid may be carried out using a nanocarbon paste electrode. The catechol may be dissolved in solution or may be dissolved into the nanocarbon paste electrode. The characterization of the reaction between catechol and antioxidants, e.g. glutathione, cysteine, homocysteine and ascorbic acid may be carried out using cyclic voltammetry at a scan rate of about $100\ mVs^{-1}$. The relationship between peak current and the total concentration of the oxidants may be given by Io (μA)=2.409+ 0.0088[antioxidants](μM), wherein Io is the oxidation peak current. The concentration of the catechol dissolved in the paste may range from about 0.01 to about 1%. The ratio between the oxidation peak current and the reduction peak current (Io/Ir) determined from cyclic voltammetry may be used to determine the concentration of antioxidants. For example, the total concentration of antioxidants (e.g. glutathione, cysteine, homocysteine and ascorbic acid) may be determined by the following relationship (Io/Ir (μA)=1.79+ 0.11[antioxidants](μM)).

Cylic voltammetry may be employed to detect both homocysteine and glutathione using a catechol solution with the CNT-GCE. This may be achieved using a combination of high and low scan rates. For example a scan rate of at least about 500 mVs$^{-1}$ can first be applied followed by a scan rate of about 50 mVs$^{-1}$ or less with cyclic voltammetry being measured at both scan rates. The concentration of homocysteine may be determined using the peak current at the higher scan rate using the analytical curve for this scan rate, for example I(μA)=(0.0478+/−0.0113) [HCys](μM). The homocysteine concentration may be used to calculate the peak current at the lower scan rate using a different curve, for example I(μA)=(0.0250+/−0.00077) [HCys](μM). This value may be subtracted from the value associated with the total adduct peak current at the low scan rate thus providing the current for the glutathione-catechol reaction. The glutathione concentration may then be determined using another appropriate calibration curve, for example at 50 mVs$^{-1}$, for example I(μA)=(0.0146+/−0.00030) [GSH](μM). The individual concentrations of glutathione and homocysteine may be each determined when both present in a given sample and optionally when cysteine and/or ascorbic acid are present.

BRIEF DESCRIPTION OF THE FIGURES

The invention will now be described, by way of example only and without limitation, with reference to the following Figures and Examples, in which.

μM, (d) 20 μM, (e) 40 μM, (f) 80 μM and (g) 100 μM using nanocarbon paste electrode. v=100 mVs$^{-1}$. Inset: analytical curve.

Figure 27:
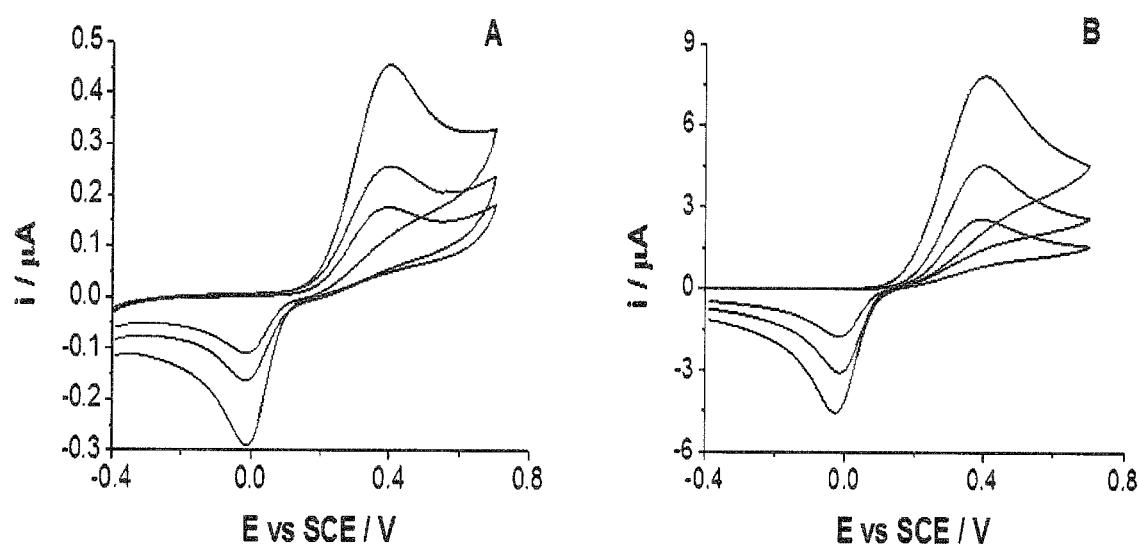

FIG. 27: Cyclic voltammetric responses for 0.05% (A) and 0.3% (B) catechol dissolved in the nanocarbon paste in PBS (pH=7.5) at 100 mVs$^{-1}$. Three scans with the same paste.

Figure 28:
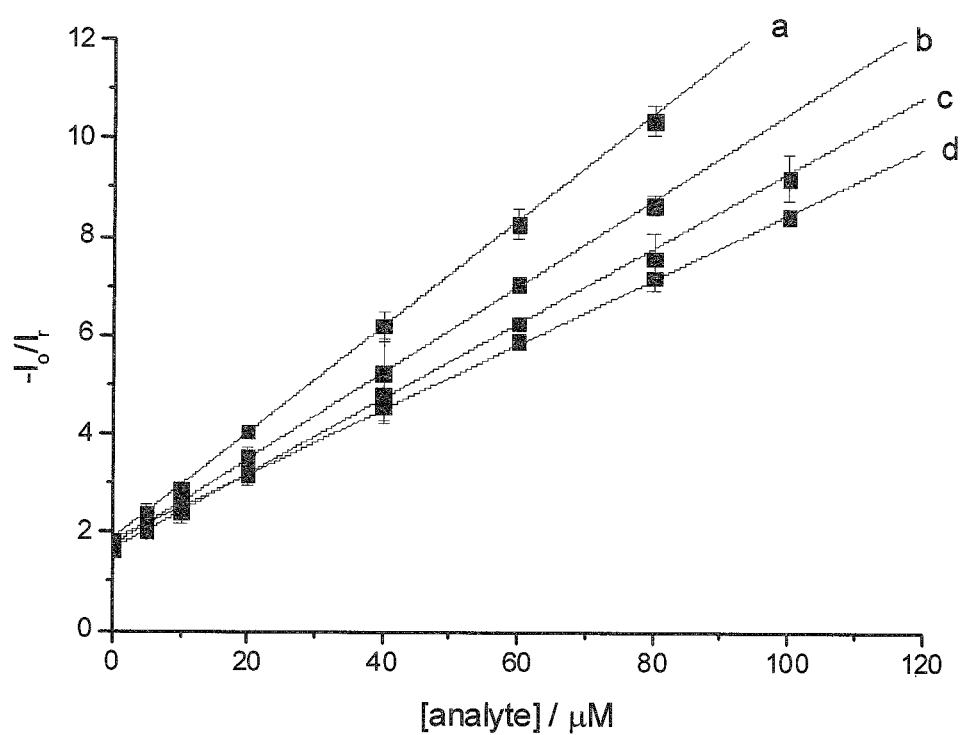

FIG. 28: Calibration curve for (a) cysteine, (b) homocysteine, (c) glutathione and (d) ascorbic acid using nanocarbon-catechol paste electrode.

Figure 29:
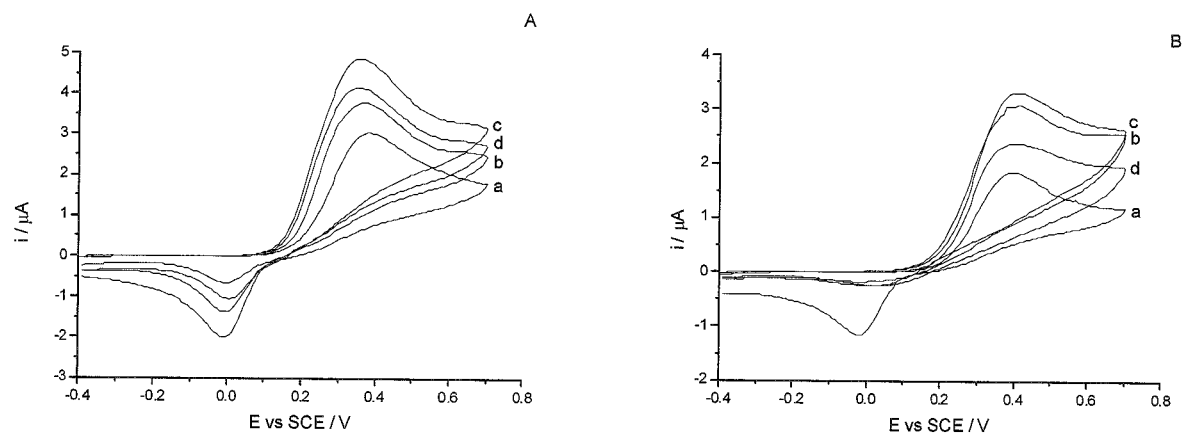

FIG. 29: Cyclic voltammetric responses in PBS (pH=7.5) in the absence (a) and presence of 40 μM "mix" (A) and 80 μM "mix" (B) using 0.3% catechol dissolved in nanocarbon paste electrode. Curves b, c and d: "mix" A, C and I, respectively.

Figure 30:
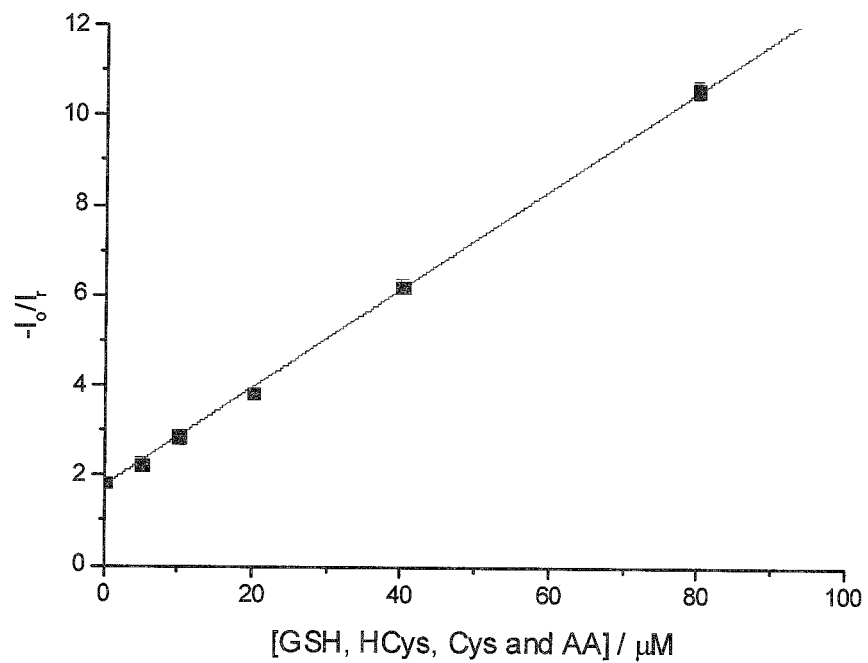

FIG. 30: Calibration curve for total antioxidants using nanocarbon-catechol paste electrode.

EXAMPLES

Example 1: Selective Electrochemical Detection of Homocysteine in the Presence of Glutathione, Cysteine, and Ascorbic Acid Using Carbon Electrodes Reagents All reagents were purchased through Sigma-Aldrich and Lancaster Synthesis at their highest available purity and were used as received without any further purification steps; catechol (99%, Aldrich), glutathione (98%, Sigma-Aldrich), D,L-cysteine (97%, Lancaster Synthesis), D,L-homocysteine (≥95%, Sigma), and ascorbic acid (99%, Aldrich). The bamboo-like multi-walled carbon nanotubes, MWCNT (30±10 nm diameter, 5-20 μM length, >95% purity) were purchased from Nanolab, Waltham, Mass., USA. The bamboo-like carbon nanotubes were characterized by the manufacturer using transmission electron microscopy (TEM). All solutions were prepared with deionized water at a resistivity of no less than 18.2 MΩ cm$^{-1}$ at 25° C. (Millipore, UK). The buffer solutions, 0.15 M, were prepared using potassium monohydrogen phosphate ($K_2HPO_4$) (≥98%, Sigma-Aldrich), potassium dihydrogen phosphate ($KH_2PO_4$) (≥99%, Sigma-Aldrich), and potassium hydroxide (KOH) (≥85%, Sigma-Aldrich) accordingly to the required pH range. All buffer solutions were freshly made prior to experiments with supporting electrolyte of 0.10 M potassium chloride (KCl) (99%, Sigma-Aldrich) added to each solution.

Apparatus

The electrochemical experiments in Example 1 were carried out in a three electrode system using a saturated calomel electrode, SCE, reference electrode (Hach Lange, UK), a platinum mesh 99.99% (Goodfellow, UK) counter electrode, and a glassy carbon electrode, GCE, (CH Instruments, USA) working electrode. The GCE was used as the basis for preparing the modified electrode which will be discussed later herein. The surface area of the bare glassy carbon electrode was 0.071 cm$^2$. All experiments were conducted using a computer controlled potentiostat, PGSTAT 101 (ECO-chemie, NL). A temperature controlled bath was also used to ensure that all electrochemical experiments were carried out at (20±2) ° C. in a Faraday cage. All pH measurements were conducted using a pH213 Microprocessor pH meter (Hanna instruments, UK). The pH meter was calibrated using Duracal buffers of pH 4.01±0.01, pH 7.00±0.001, and pH 10.01±0.01 (Hamilton, CH).

Preparation of Modified Carbon Nanotube Glassy Carbon Electrode (CNT-GCE)

The modification of the GCE electrode was freshly undertaken at the start of each experiment. The GCE was first polished with sequentially 3.0, 1.0, and 0.1 μm diamond spray (Kemet, UK) then rinsed with ethanol and de-ionized water. Afterwards, the carbon nanotubes were immobilized onto the surface of the glassy carbon electrode through the drop casting method. The drop casting method consisted essentially of dropping an aliquot of a CNT-ethanol suspension (0.1 mg/mL) over the surface of the GCE. This allowed the ethanol to evaporate at room temperature thus leaving a layer of CNT at the electrode surface. To ensure a full suspension of the CNT-ethanol, the solution was briefly sonicated using a sonication bath prior to drop casting. A total of 6.0 μg of CNT was drop casted onto the GCE during the modification of the electrode. The surface area of the modified CNT-GCE was obtained by cyclic voltammetry at different scan rates, ranging from 25 mVs$^{-1}$ to 400 mVs$^{-1}$, in 1.0 mM hexaammineruthenium(III) chloride and 0.1 M potassium chloride solution. The calculated average surface area for the CNT-GCE was (0.23±0.02) cm$^2$.

Screen Printed Electrodes

The use of multi-walled carbon nanotube screen printed electrodes, CNT-SPE, and graphite screen printed electrodes, G-SPE, were undertaken. The disposable screen printed electrodes were acquired from DropSens (Spain) which has a ceramic substrate consisting of a multi-walled carbon nanotube or graphite working electrode, a carbon counter electrode and a silver reference electrode. The characterization using scanning electron microscopy (SEM) of these screen printed electrodes can be found on the DropSens website.

Electrochemical Characterisation of Catechol

Cyclic voltammograms of the system were taken at different scan rates ranging from 25 mVs$^{-1}$ to 400 mVs$^{-1}$ in PBS, pH7.0 at 20° C. (FIG. 2) to initially characterize the electrochemical behaviour of 0.1 mM catechol using both CNTs-GCE and GCE. The voltammogram shows the redox process of catechol at $E_{1/2}$=+0.15 V (vs. SCE). This is attributed to the two electron, two proton oxidation of the catechol to the corresponding ortho-quinone species:

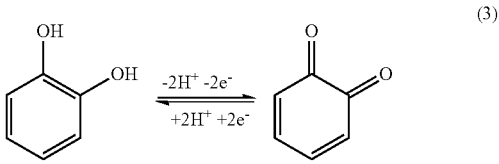 [SMILES: Oc1ccccc1O ; O=C1C=CC=CC1=O]

(3)

Figure 2:
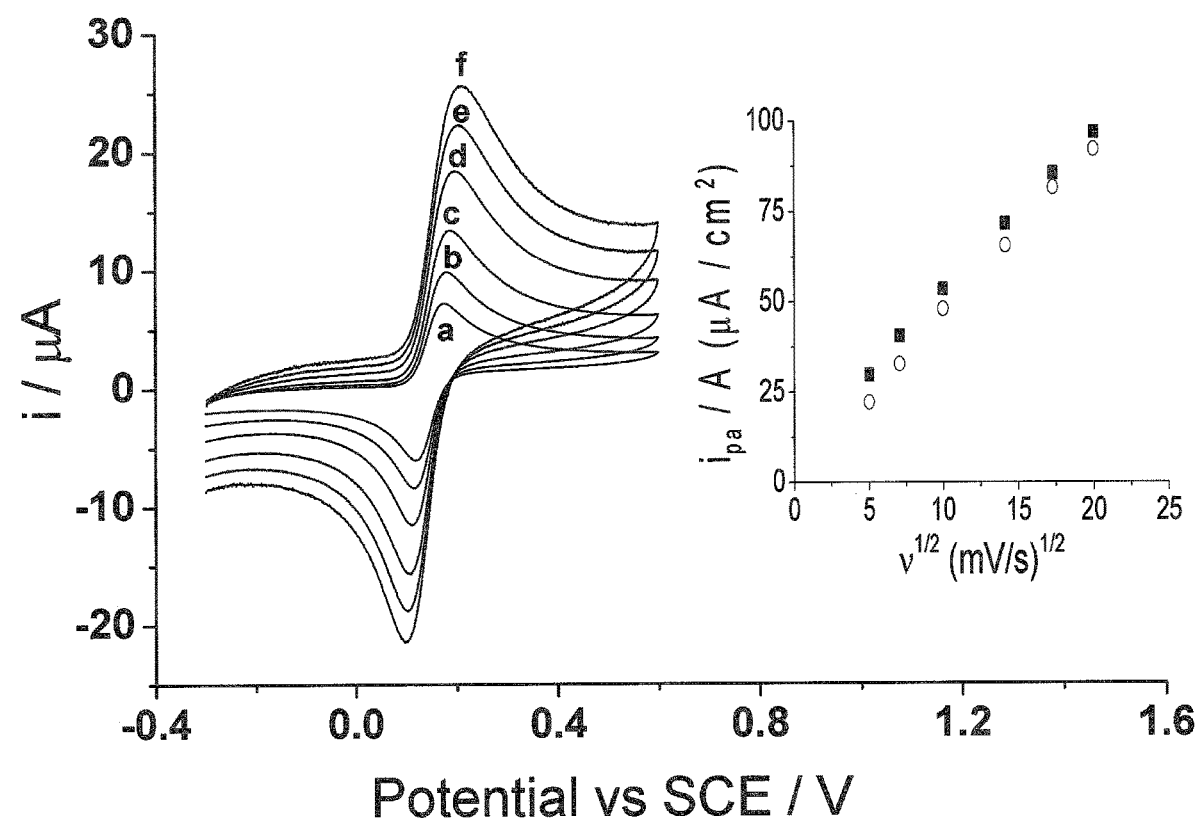
FIG. 2: Cyclic voltammograms of CNT-GCE in 0.1 mM catechol (PBS, pH 7.0) at 20° C. a.) 25 mV s$^{-1}$ b.) 50 mV s$^{-1}$ c.) 100 mV s$^{-1}$ d.) 200 mV s$^{-1}$ e.) 300 mV s$^{-1}$ f.) 400 mV s$^{-1}$. Inset: peak current, $i_{pa}$, vs. square root of scan rate, $v^{1/2}$. ■ CNT-GCE and ○ GCE.

The inset in FIG. 2 shows that there is a linear correlation when the peak current, $i_p$, is plotted with the square root of scan rate, $v^{1/2}$, suggesting a diffusional process of catechol at either electrode. The diffusion coefficient was estimated using the Randle-Ševčik equation, as being (7.0±1.0)×10$^{-6}$ cm$^2$ s$^{-1}$ for the CNTs-GCE and 7.5×10$^{-6}$ cm$^2$ s$^{-1}$ for GCE.

Catechol Electrochemical Characterisation in the Presence of Homocysteine

Figure 3:
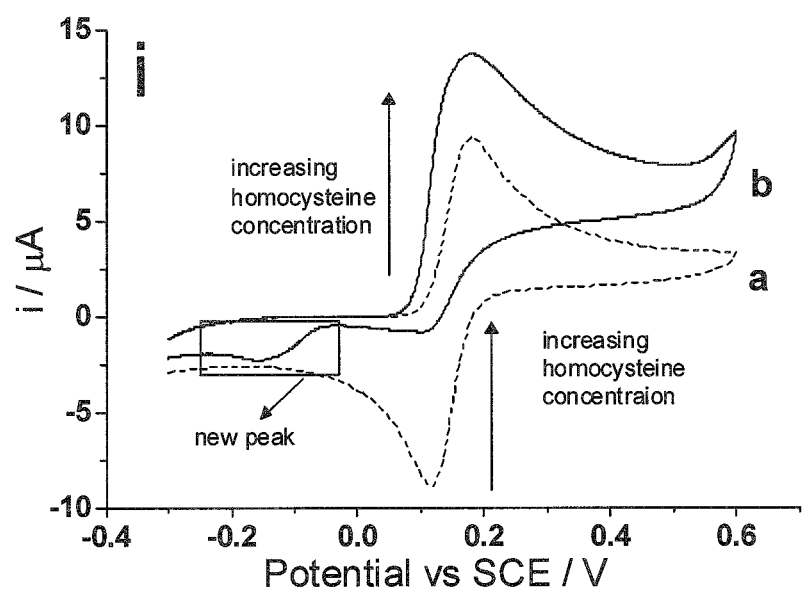
FIG. 3: Cyclic voltammograms (50 mVs$^{-1}$, pH 7.0 phosphate buffer) illustrating the 0.1 mM catechol response in an absence (dotted) and presence of 0.1 mM homocysteine (solid) at the i.) CNT-GCE and ii.) GCE.
Figure 3:
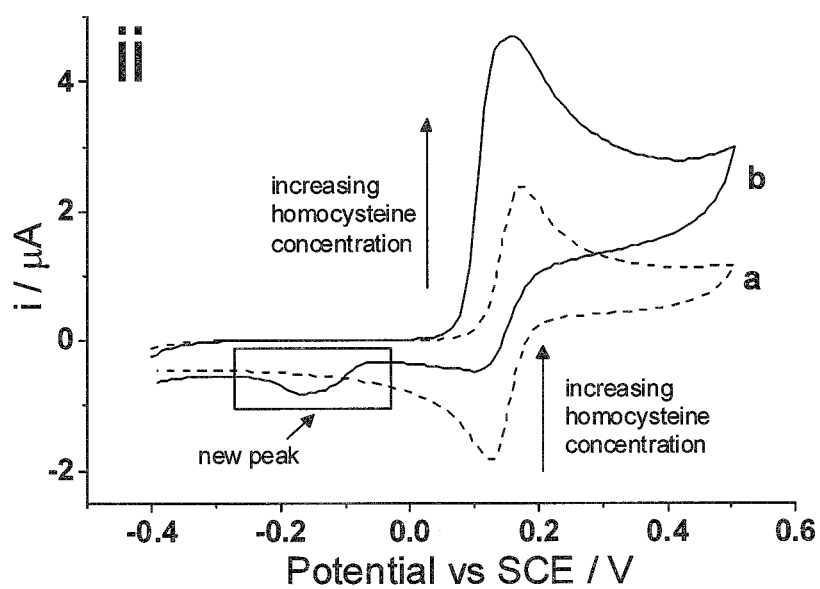

Cyclic voltammetry (50 mVs$^{-1}$) was used to observe the electrochemical response of 0.1 mM catechol (pH 7.0, PBS) in the presence of HCys. FIG. 3 shows the comparison of the voltammetric response of the catechol in the absence (dotted line) and presence (solid line) of 0.1 mM HCys at the CNTs-GCE (i) and GCE (ii). In the presence of HCys, the voltammogram shows the forward peak increases as the back peak decreases and a new product peak emerges at ca.

−0.20 V (vs. SCE). This peak is due to the reduction of substituted catechol molecule, as described above in Scheme (2).

Electrochemical Detection of Homocysteine

Figure 4:
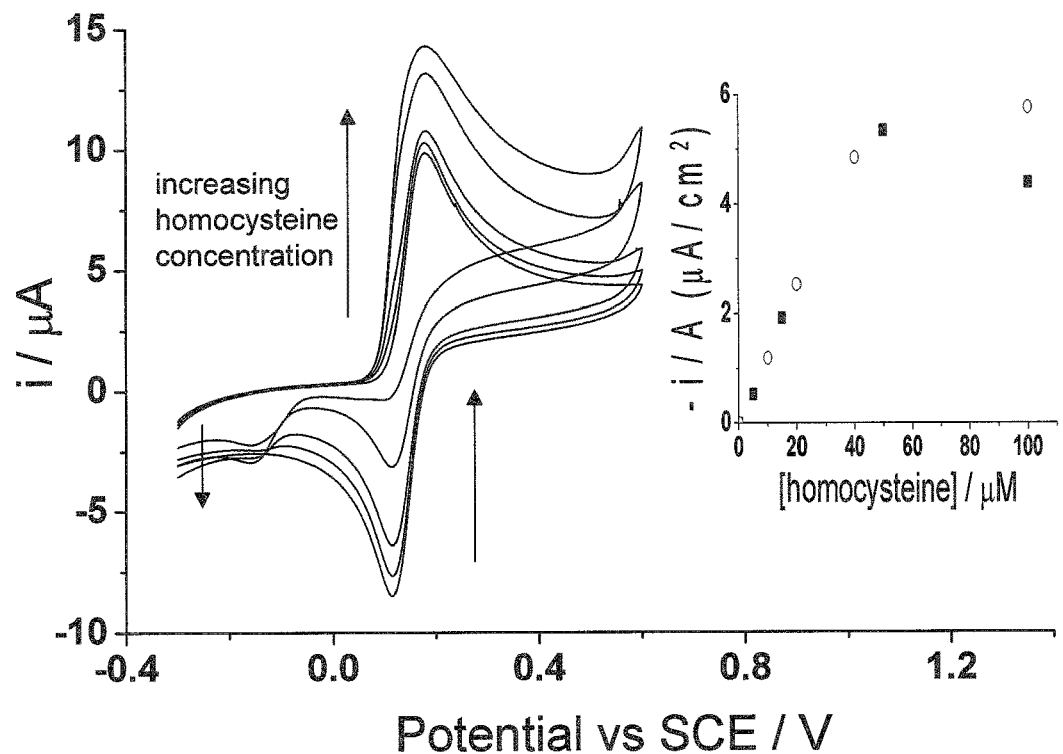
FIG. 4: Cyclic voltammograms (50 mVs$^{-1}$, pH 7.0 phosphate buffer) illustrating the 0.1 mM catechol response to homocysteine concentrations ranging from 0-0.1 mM. Inset: peak current of the new peak plotted against the concentration of homocysteine. ■ CNT-GCE and ○ GCE.

To observe the electrochemical behaviour of catechol with different concentrations of homocysteine, cyclic voltammetry (scan rate of 50 mVs$^{-1}$) was carried out with a solution containing 0.1 mM catechol at varying homocysteine concentrations ranging from 0-0.1 mM. FIG. 4 shows that as the concentration of homocysteine increases, the forward and new product peak, ca. −0.20 V (vs. SCE), increases as the back peak decreases. When the peak current of the new product peak is plotted with concentration of homocysteine (FIG. 4 inset), the linear trend increases up to 60 μM and then decreases at 0.1 mM homocysteine. The systematically increasing trend indicates that homocysteine may be detected.

Figure 5:
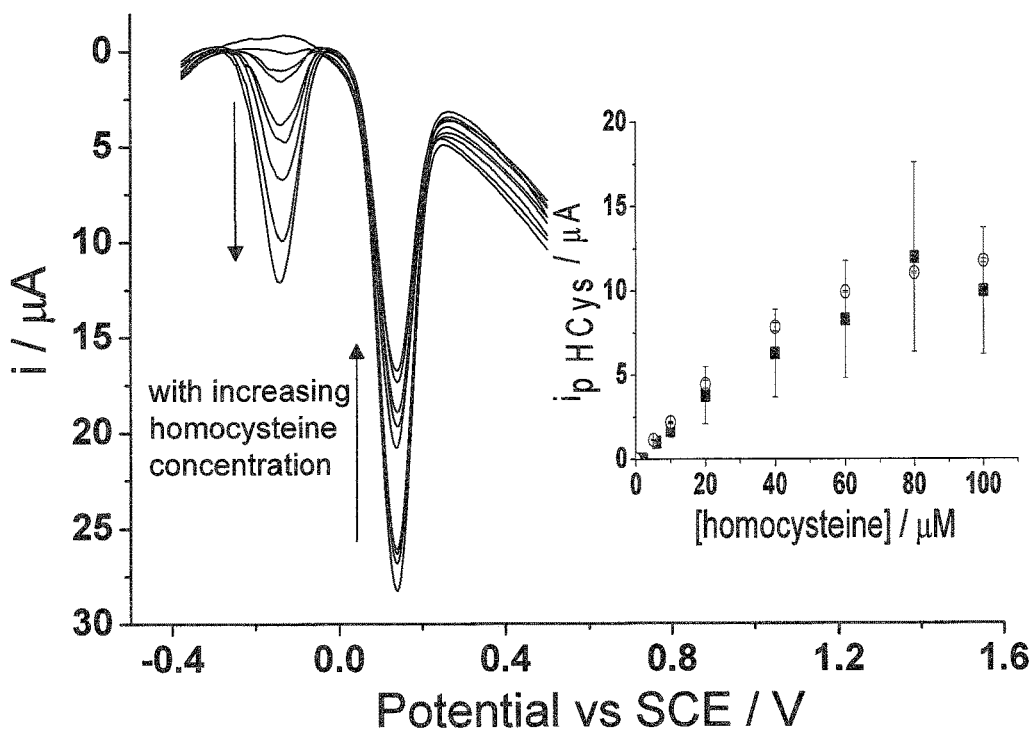
FIG. 5: Square wave voltammetry response of 0.1 mM catechol at the CNT-GCE with varying concentration of homocysteine (PBS, pH 7.0) ranging from 0-0.1 mM. Inset: Peak current at ca. −0.20 V (vs. SCE) plotted against concentration of homocysteine. ■ CNT-GCE and ○ GCE.

To increase the sensitivity of HCys detection in the presence of 0.1 mM catechol (PBS, pH 7.0), square wave voltammetry was utilized. The parameters were optimized for CNT-GCE and GCE at frequency 50 Hz, step potential 4.0 mV, and amplitude 50 mV. FIG. 5 shows the square wave voltammograms of the catechol response to different concentrations of homocysteine at the CNT-GCE as a similar response at GCE was observed. The results obtained with square wave voltammetry were consistent with the results obtained with cyclic voltammetry for both electrodes; where the catechol peak (ca. +0.14 V vs. SCE) decreases and the new product peak at ca. −0.20 V (vs. SCE) emerges and grows with increasing homocysteine concentration. There is a linear relationship when the peak current of the product, ca. −0.20 V (vs. SCE), is plotted with concentration of homocysteine. For CNT-GCE, the linear relationship is $I(\mu A)=0.2[HCys](\mu M)$ with concentrations up to 80 μM (FIG. 5 inset) and the limit of detection (LOD) was determined to be 120 nM. For GCE, the linear relationship is $I(\mu A)=0.2[HCys](\mu M)$ at homocysteine concentration up to 40 μM and a determined LOD of 90 nM.

Interference Studies

In connection with the use of homocysteine detection in authentic biological samples and media, the selectivity of the system was next investigated at each electrode. First, an individual assay with 0.1 mM catechol (PBS, pH 7.0) was done with the separate additions of 0.1 mM of each antioxidant: glutathione (GSH), cysteine (Cys), and ascorbic acid (AA) at each CNT-GCE and GCE. These antioxidants were chosen because they are commonly found in biological samples at high concentrations. In addition, 0.1 mM of each analyte was used to present the worst-case scenario of possibly having abnormally high concentrations present in biological samples.

Interference Study at the Glassy Carbon Electrode (GCE)

Figure 6:
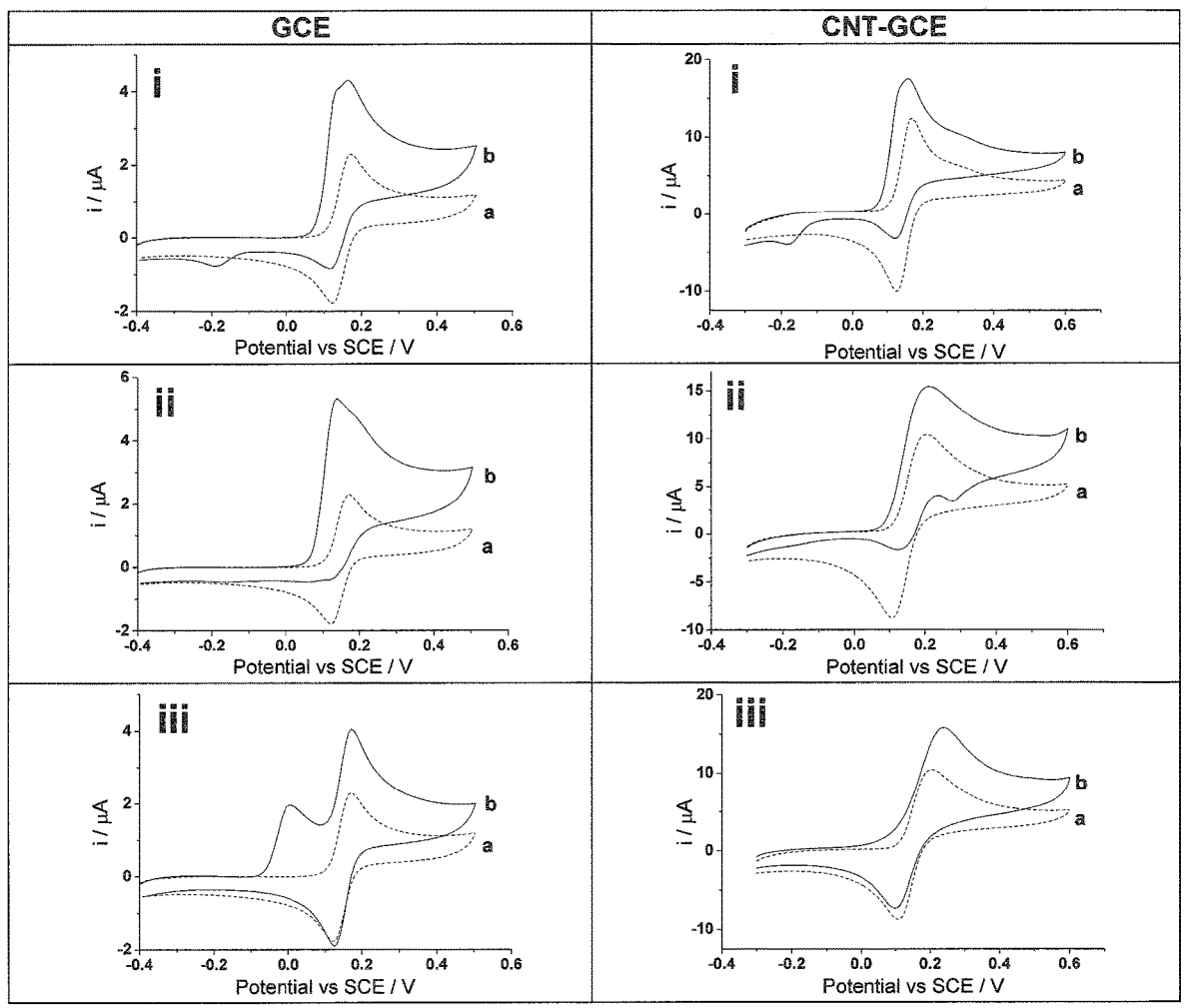
FIG. 6: Cyclic voltammograms (50 mVs$^{-1}$, pH 7.0 PBS) for 0.1 mM catechol in an absence (a) and presence (b) of 0.1 mM concentration of i.) glutathione ii.) cysteine iii.) ascorbic acid at CNT-GCE and GCE.

Cyclic voltammograms (50 mVs$^{-1}$) were taken of 0.1 mM catechol (PBS, pH 7.0) solutions containing 0.1 mM of each GSH, Cys, and AA. FIG. 6 shows a cyclic voltammogram comparison in the absence (curve a) and presence (curve b) of these antioxidants: GSH (i), Cys (ii) and AA (iii) reacting with catechol. For GSH and Cys, the voltammograms show the forward peak increases and back peak decreases but only in the case with GSH, a new peak emerges at ca. −0.20 V (vs. SCE) due to the catechol-thiol interaction favoring the 1,4-Michael addition reaction. In the case with the catechol interaction with Cys at the GCE, the favoring reaction appears to be electrocatalytic at the GCE. With AA, the voltammogram shows that the forward peak increases slightly and a new peak emerges ca. 0 V (vs. SCE) indicating that it is the oxidation of pure ascorbic acid at the GCE. Upon examining all the voltammograms, there can be difficulties measuring HCys when in the presence of GSH at GCE because the peak potentials of their adduct with oxidized quinones are close to each other.

Interference Study at the Carbon Nanotube Modified Carbon Electrode (CNT-GCE)

FIG. 6 shows the electrochemical response at each electrode of 0.1 mM catechol (dotted line) in a presence of 0.1 mM of each antioxidants (solid lines): GSH (i), Cys (ii), and AA (iii) at the CNT-GCE. Voltammograms show an increase in forward peak with a decrease in the back peak for catechol reacting with GSH (i) and Cys (ii), with an introduction of a new product peak at ca. −0.200 V, and +0.300 V respectively. This introduction of a new product peak indicates a 1,4-Michael addition reaction is favoured and occurs with the thiols at the CNT-GCE. While there was no new product peak for the presence of ascorbic acid, the voltammograms show a slight increase in the forward peak which is similarly seen with GCE. By examining the peak potentials of the new product peak, the presence of glutathione can be a possible interference towards the detection of homocysteine as the product peak potentials are close to each other. For the case with cysteine, the product peak emerges at a different peak potential further away from the reaction with homocysteine and glutathione. It is considered that the catechol reaction with each different thiol reacts to form a new electrochemical species different from each other thus having different peak potentials.

Homocysteine Selectivity

Figure 7:
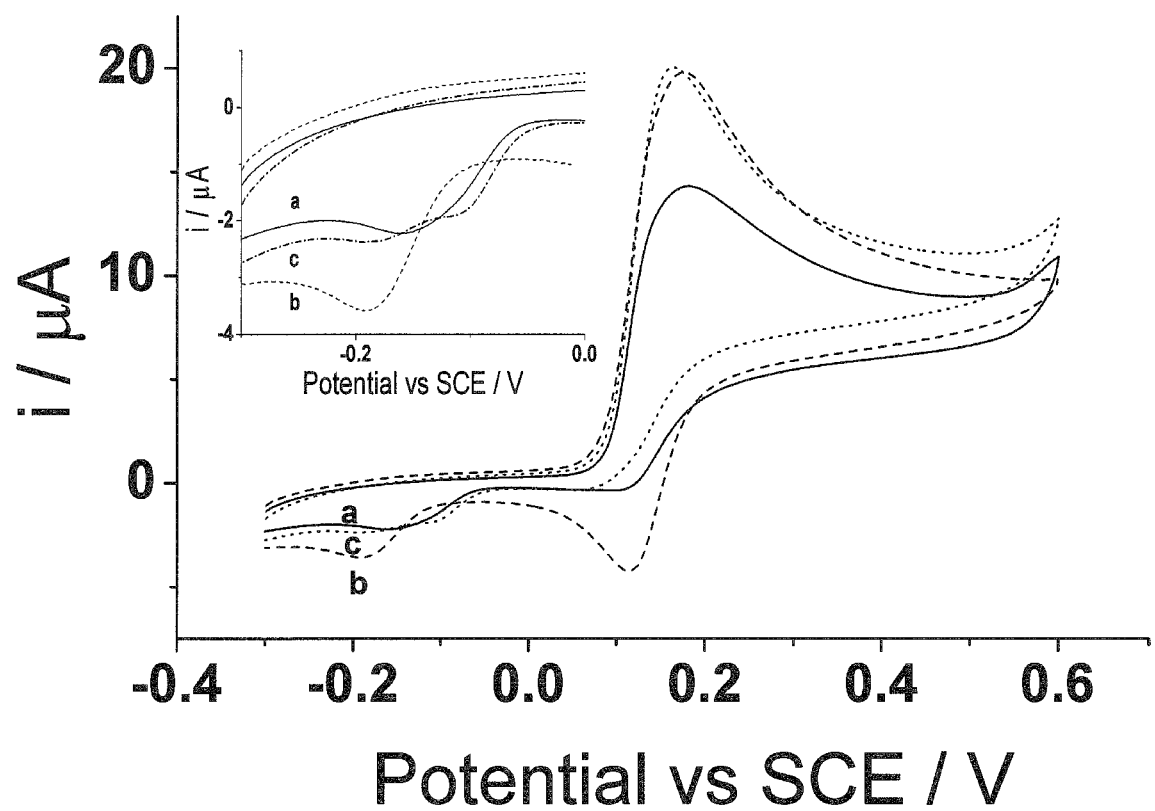
FIG. 7: Cyclic voltammograms (50 mVs$^{-1}$, pH 7.0 PBS) at CNT-GCE of 0.1 mM catechol containing (a) 0.1 mM homocysteine (b) 0.1 mM glutathione and (c) 0.1 mM homocysteine and glutathione.

FIG. 7 shows the behaviour of catechol in the presence of homocysteine (curve a), glutathione (curve b), and both (curve c) at 50 mVs$^{-1}$, similar behaviour is also seen at GCE. In the presence of both HCys and GSH (FIG. 7c); the new product peaks for both analytes are close which makes it difficult to determine changes in peak current between the two analytes, if it should occur. As an attempt to optimize the single homocysteine signal, one proposed method can be to take advantage of the different molecular size and reaction rates of either analytes with catechol. A higher scan rate may be applied to outrun the glutathione-catechol reaction which still allows the homocysteine-catechol interaction to take place.

Figure 8:
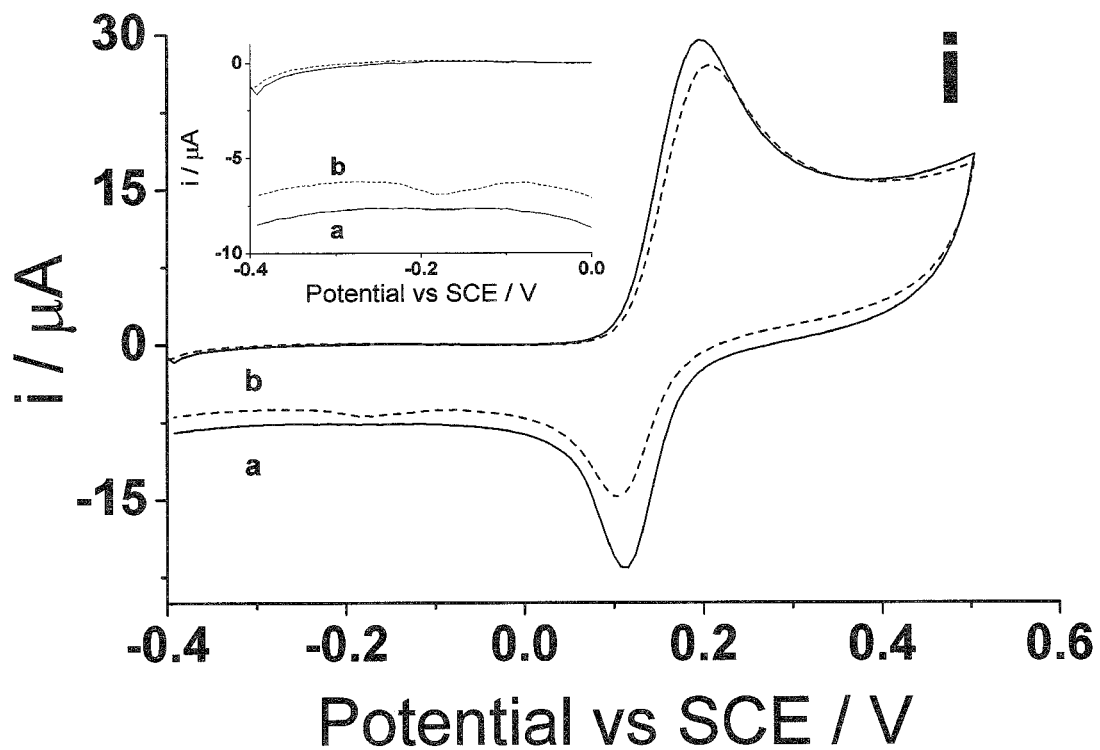
FIG. 8: Cyclic voltammograms at i.) GCE (at 1.5 Vs$^{-1}$) and ii.) CNT-GCE (at 500 mVs-1) of 0.1 mM catechol containing (a) 0.1 mM glutathione and (b) 0.1 mM homocysteine (PBS, pH 7.0).
Figure 8:
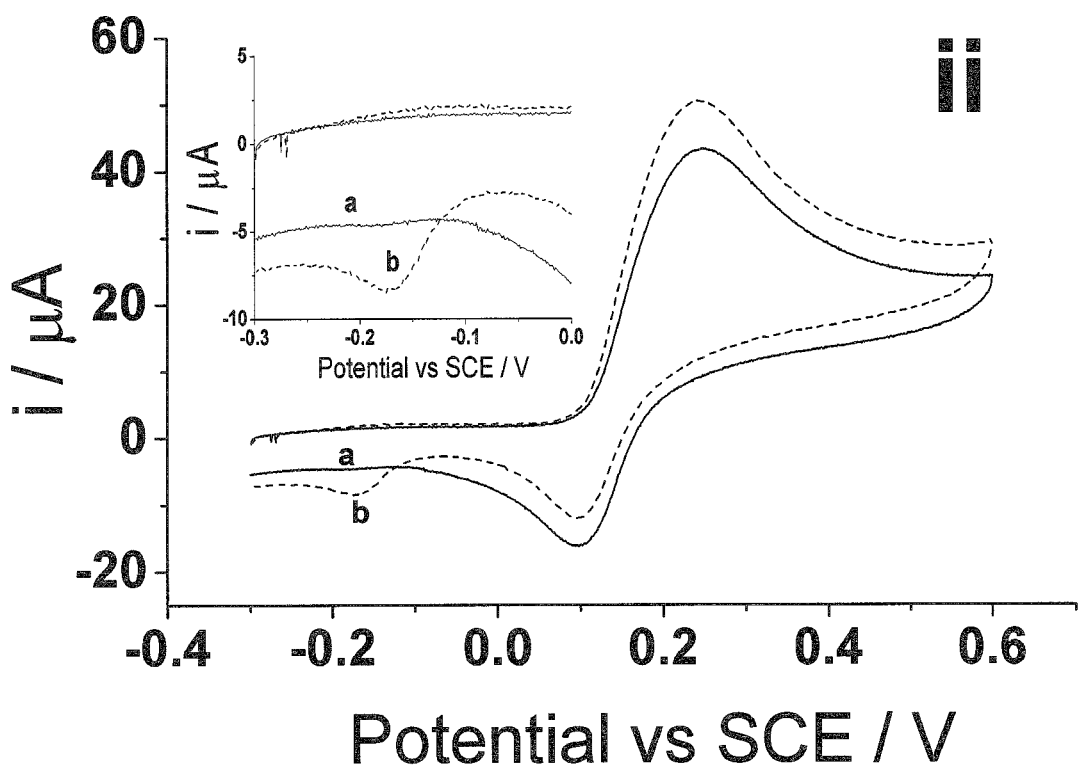

FIG. 8 shows cyclic voltammetry at an optimum scan rate at 1.5 Vs$^{-1}$ for GCE (i) and 500 mVs$^{-1}$ for CNTs-GCE (ii) was found and applied to a catechol solution with the presence of glutathione (curve a) and homocysteine (curve b) (PBS, pH 7.0) separately to see the possibility of homocysteine selectivity. There is no significant signal for the product peak of the glutathione-catechol reaction (curve a) while for the homocysteine-catechol reaction (curve b), the product peak (ca. −0.20 V vs. SCE) emerges for both systems. This indicates that homocysteine may be detected in the presence of glutathione at the higher scan rate. AA and Cys were not interferences to the homocysteine product signal and homocysteine may be detected in the presence of AA, Cys and GSH using cyclic voltammetry.

Figure 9:
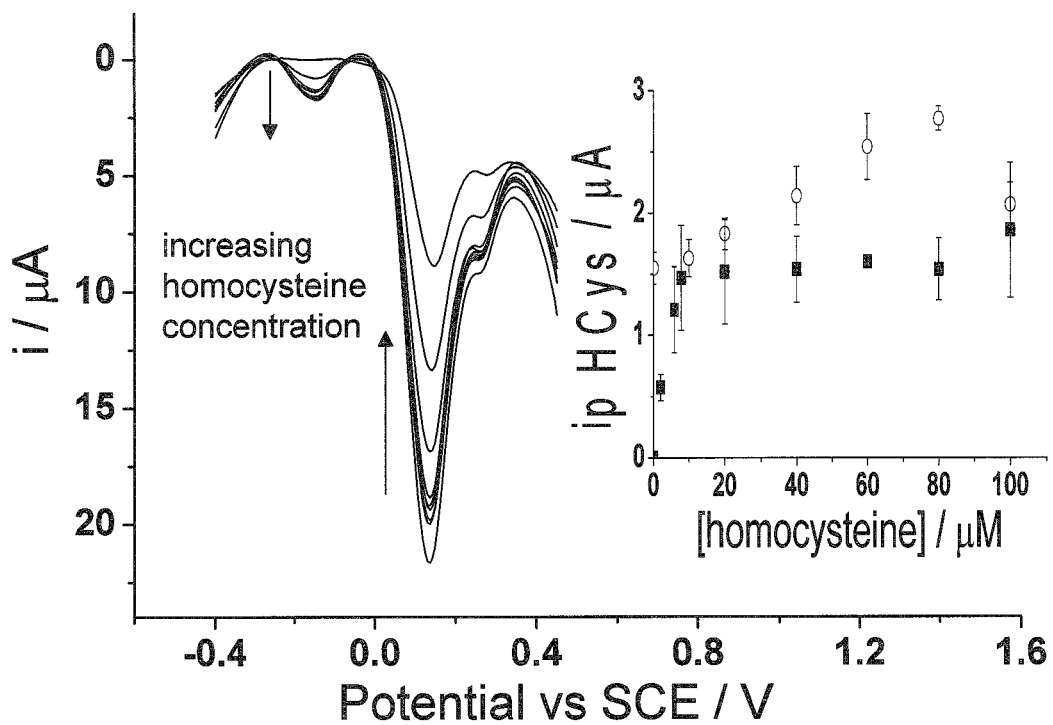
FIG. 9: Square wave voltammograms of CNT-GCE in solution containing 0.1 mM glutathione-cysteine-ascorbic acid-catechol with varying homocysteine concentration (0-0.1 mM) at 20° C. Inset: Homocysteine peak current at ca. −0.20 V (vs. SCE) plotted against concentration of homocysteine. ■ CNT-GCE and ○ GCE.

Square wave voltammetry (optimized for CNT-GCE at frequency 50 Hz, amplitude 50 mV, and step potential 10 mV and GCE at frequency 50 Hz, amplitude 75 mV, and step potential 30 mV) was applied to a solution containing various HCys concentrations, 0-0.1 mM, in the presence of 0.1 mM for each of catechol, GSH, Cys, and AA. FIG. 9 shows the square wave voltammograms of different homocysteine concentrations in the presence of cysteine, glutathione and ascorbic acid at the CNT-GCE. The inset to FIG. 9 shows the homocysteine-catechol product current peak increases with homocysteine concentration at both electrodes. Homocysteine selectivity was not achieved at GCE under the optimized square wave voltammetry parameters presented because the result shows a signal in the absence of homocysteine due to catechol-glutathione product. While the selectivity of homocysteine was successfully achieved at CNT-GCE as no signal appeared in the absence of homocysteine when the other antioxidants are present. The differences in selectivity can be rationalized by the diffusion changes at the electrode surfaces, bare glassy carbon electrode versus porous layer of carbon nanotube modified electrode. Therefore, the CNT-GCE is the best electrode to obtain selective homocysteine detection in the presence of glutathione, cysteine and ascorbic acid.

Sensitivity of homocysteine at CNT-GCE obtained in the presence of these analytes, at the range 0-10 µM, is (0.20±0.02) µA µM$^{-1}$ and the limit of detection is determined to be 660 nM. The narrow working range may be due to the antioxidants present; including homocysteine, undergoing a competition reaction with the available catechol in solution. In spite of the antioxidant present undergoing a reaction we can still observe no change in peak current up to 10 µM homocysteine in the presence of 0.1 mM analytes. However, there is a possibility that the dynamic range might be extended if those concentrations were lower.

Homocysteine Detection Using Carbon Nanotube Screen-Printed Electrodes

Figure 10:
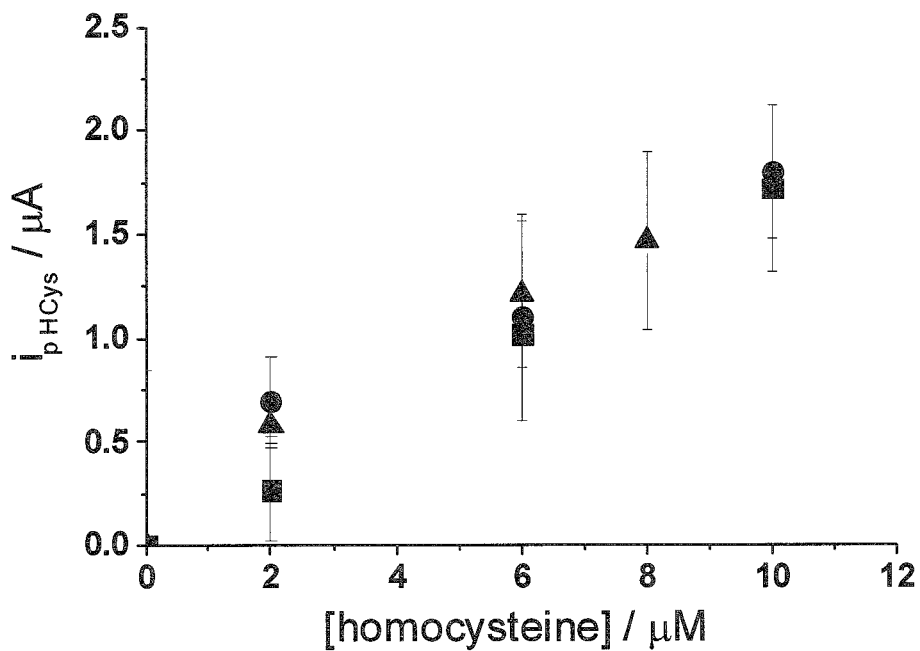
FIG. 10: Calibration plot of detection of homocysteine (pH 7.0, PBS at 20° C.) with 0.1 mM catechol present in solution at ■ CNT-GCE. Homocysteine detection in the presence of cysteine, glutathione, and ascorbic acid (PBS, pH 7.0 at 20° C.) at ● CNT-GCE, ▲ CNT-SPE.

The use of commercially available carbon nanotube screen-printed electrodes, CNT-SPE, was applied to this system. CNT-SPE was tested in a solution containing 0.1 mM of catechol and all of the other analytes mentioned above while varying the concentration of homocysteine (pH 7.0, PBS) at 20° C. To ensure the same potential and conditions used previously, SCE was used as the reference electrode in the testing for comparison to the CNT-GCE. FIG. 10 shows a calibration curve of the tested CNT-SPE plotted in comparison with the other calibration curves of homocysteine concentration up to 10 µM. The figure shows the linear range, 0-10 µM, using CNT-SPE, is similar to CNT-GCE in the presence of the other analytes. The sensitivity for HCys at CNT-SPE is (0.20±0.02) µA µM$^{-1}$ which is the same in the absence and presence of the analytes at CNT-GCE. Graphite screen-printed electrode was also applied to the same system. However, a signal appeared in the absence of homocysteine due to catechol-glutathione product showing that homocysteine selectivity is not possible under these conditions. The commercially available carbon nanotube screen printed electrodes was therefore shown to be applicable towards homocysteine detection.

Example 1 illustrates that the use of an electrochemically generated ortho-quinone facilitates the reaction of the thiol containing compound, homocysteine, on carbon electrodes. The detection of pure homocysteine may take place using two different carbon electrodes, bare glassy carbon electrode and carbon nanotube modified carbon electrode. The selective detection of homocysteine was achieved using a carbon nanotube modified electrode with a sensitivity of (0.20±0.02) µA µM$^{-1}$ and a limit of detection 660 nM at a linear range of 0-10 µM in the absence and presence of other antioxidants: glutathione, ascorbic acid, and cysteine. In addition, the use of commercially available carbon nanotube screen printed electrodes was applied and it was shown that these can be applicable towards facile, fast and disposable electrodes for homocysteine detection.

Example 2: Simultaneous Electrochemical Detection of Homocysteine and Cysteine in the Presence of Ascorbic Acid and Glutathione Using a Nanocarbon Modified Electrode Reagents All reagents were purchased through Sigma-Aldrich and Lancaster Synthesis at their highest available purity and were used as received without any further purification steps; catechol (99%, Aldrich), glutathione (98%, Sigma-Aldrich), D,L-cysteine (97%, Lancaster Synthesis), D,L-homocysteine (≥95%, Sigma), and ascorbic acid (99%, Aldrich). The nanocarbon (14±10 nm in diameter) was obtained from Cabot Corporation (Billerica, Mass., USA). The characterization of the nanocarbon was previously characterized using scanning electron microscopy (SEM). All solutions were prepared with deionized water at a resistivity of no less than 18.2 MΩ cm$^{-1}$ at 25° C. (Millipore, UK). The buffer solutions, 0.15 M, were prepared using potassium monohydrogen phosphate ($K_2HPO_4$) (≥98%, Sigma-Aldrich), potassium dihydrogen phosphate ($KH_2PO_4$) (≥99%, Sigma-Aldrich), and potassium hydroxide (KOH) (85%, Sigma-Aldrich) accordingly to the required pH range. All buffer solutions were freshly made prior to experiments with supporting electrolyte of 0.10 M potassium chloride (KCl) (99%, Sigma-Aldrich) added to each solution.

Apparatus

The electrochemical experiments were carried out in a three electrode system using a saturated calomel electrode, SCE, reference electrode (Hach Lange, UK), a glassy carbon electrode, GCE, (CH Instruments, USA) working electrode and a platinum mesh 99.99% (Goodfellow, UK) counter electrode. The surface area of the GCE was 0.071 cm$^2$. All experiments were conducted using a computer controlled potentiostat, PGSTAT 101 (ECO-chemie, NL). A temperature controlled bath was also used to ensure that all electrochemical experiments were carried out at 20° C.±2° C. in a Faraday cage. All pH measurements were conducted using a pH213 Microprocessor pH meter (Hanna instruments, UK). The pH meter was calibrated using Duracal buffers of pH 4.01±0.01, pH 7.00±0.001, and pH 10.01±0.01 (Hamilton, CH).

Preparations of Modified Nanocarbon Modified Glassy Carbon Electrode (NC-GCE)

The modification of the nanocarbon modified glassy carbon electrode (NC-GCE) was done prior to each experiment. The GCE was polished with diamond spray (Kemet, UK) in descending order, 3.0, 1.0, and 0.1 µM respectively. Next, the polished electrode was rinsed with ethanol followed by de-ionized water. The immobilization of the nanocarbon onto the surface of the GCE is done via the drop cast method. The drop cast method is essentially taking an aliquot of a nanocarbon-ethanol suspension (1:1) and dropping onto the surface of the GCE. A layer of carbon material remains at the surface of the carbon electrode after allowing the volatile solvent to dry at room temperature. A total of 50 µg nanocarbon was used to modify the NC-GCE. The use of a sonication bath (Fisher Scientific, 230 V, 50 Hz) is recommended to ensure a full suspension of the nanocarbon-ethanol solution prior to drop casting.

Electrochemical Characterisation of Catechol on Nanocarbon Modified Glassy Carbon Electrode (NC-GCE)

Figure 11:
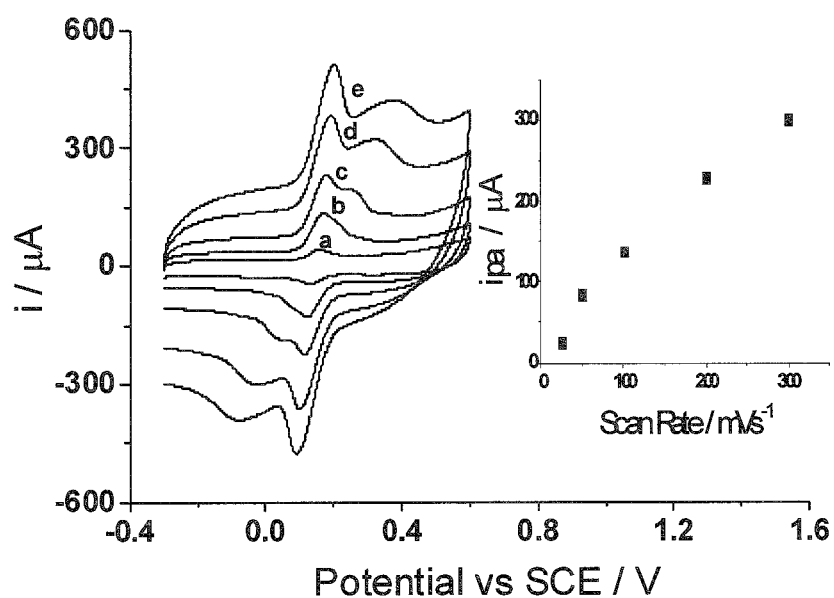
FIG. 11: Cyclic voltammograms of NC-GCE in 0.1 mM catechol (PBS, pH 7.0) at 20° C. a.) 25 mV s$^{-1}$ b.) 50 mV s$^{-1}$ c.) 100 mV s$^{-1}$ d.) 200 mV s$^{-1}$ e.) 300 mV s$^{-1}$. Inset: peak current, $i_p$, vs. scan rate, v, of CNTs-GCE.

Initial characterization of catechol using a NC-GCE was performed using cyclic voltammetry to determine the electrochemical behaviour. Cyclic voltammograms of the modified electrode were taken in a solution containing 0.1 mM catechol (PBS, pH 7.0) at 20° C. at varying scan rates, ranging from 25 mVs$^{-1}$ to 300 mVs$^{-1}$ (shown in FIG. 11). The figure shows that the catechol undergoes a redox process ca. +0.14 V (vs. SCE). This is attributed to the two electron, two proton oxidation of the catechol to the corresponding othro-quinone species, (refer to the first step in scheme (2)). The voltammograms in FIG. 11 show the catechol peak, ca. +0.14 V (vs. SCE), splits with increasing scan rate. Inspection of the inset to FIG. 11 shows that peak current, $i_p$, increases apparently linearly with voltage scan rate, v, which suggests behaviour consistent with surface confined voltammetry.

Figure 12:
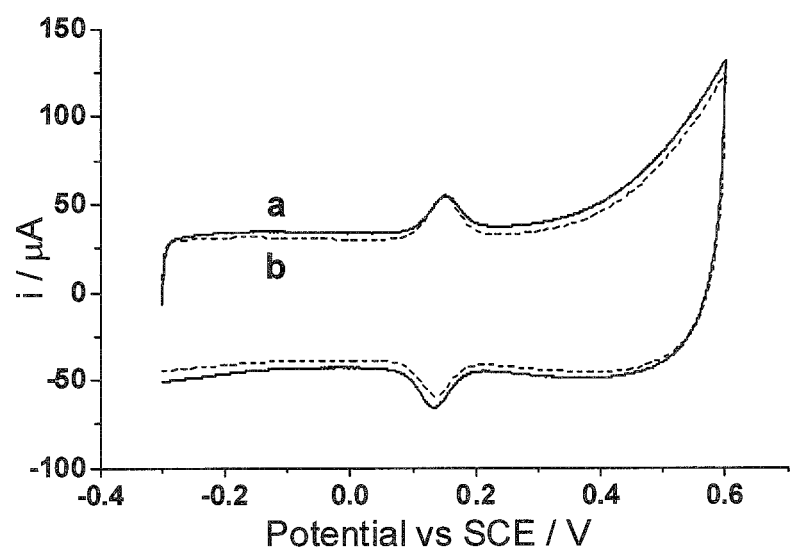
FIG. 12: Cyclic voltammograms (50 mVs$^{-1}$) NC-GCE in PBS (pH 7.0) at 20° C. of a.) 0.1 mM catechol in solution b.) dipped in 0.1 mM catechol solution prior to test.

The porous structure of nanocarbon on the NC-GCE was investigated in relation to the electrochemical response of catechol. The electrode was pretreated by dipping the NC-GCE into a solution containing 0.1 mM catechol (PBS, pH 7.0) for ca. 43 seconds. Next, the dipped electrode, CAT-NC-GCE, was transferred into PBS (pH 7.0) and a cyclic voltammetry was obtained and to compare to the NC-GCE when catechol is in solution (pH 7.0), shown in FIG. 12. The cyclic voltammograms of the NC-GCE with catechol present in solution (curve a) compared to in CAT-NC-GCE in PBS (pH 7.0) (curve b) are similar to one another. The measured peak current of the catechol in solution at the NC-GCE is (2.0±0.4) µA, and the catechol dipped NC-GCE is (2.0±0.3) µA are in good agreement with each other. Without wishing to be bound by theory, this suggests that the catechol is physisorbed onto the porous nanocarbon, which further indicates that the catechol on the NC-GCE is surface bound. It may be that the electrode can have the option of having the catechol present in solution or immobilized onto the surface of the electrode. The catechol-nanocarbon modified glassy carbon electrode, CAT-NC-GCE, was chosen as the presented electrode.

Electrochemical Characterization of Homocysteine (HCys)

Figure 13:
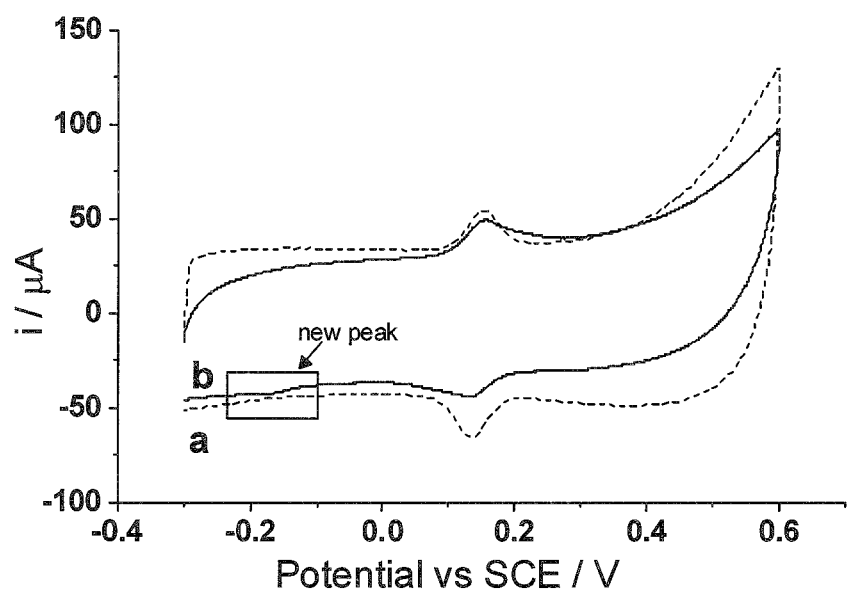
FIG. 13: Cyclic voltammogram (50 mVs$^{-1}$) of CAT-NC-GCE in a.) PBS (pH 7.0) (dotted) and b.) 0.1 mM homocysteine (solid) (pH 7.0) at 20° C.
Figure 14:
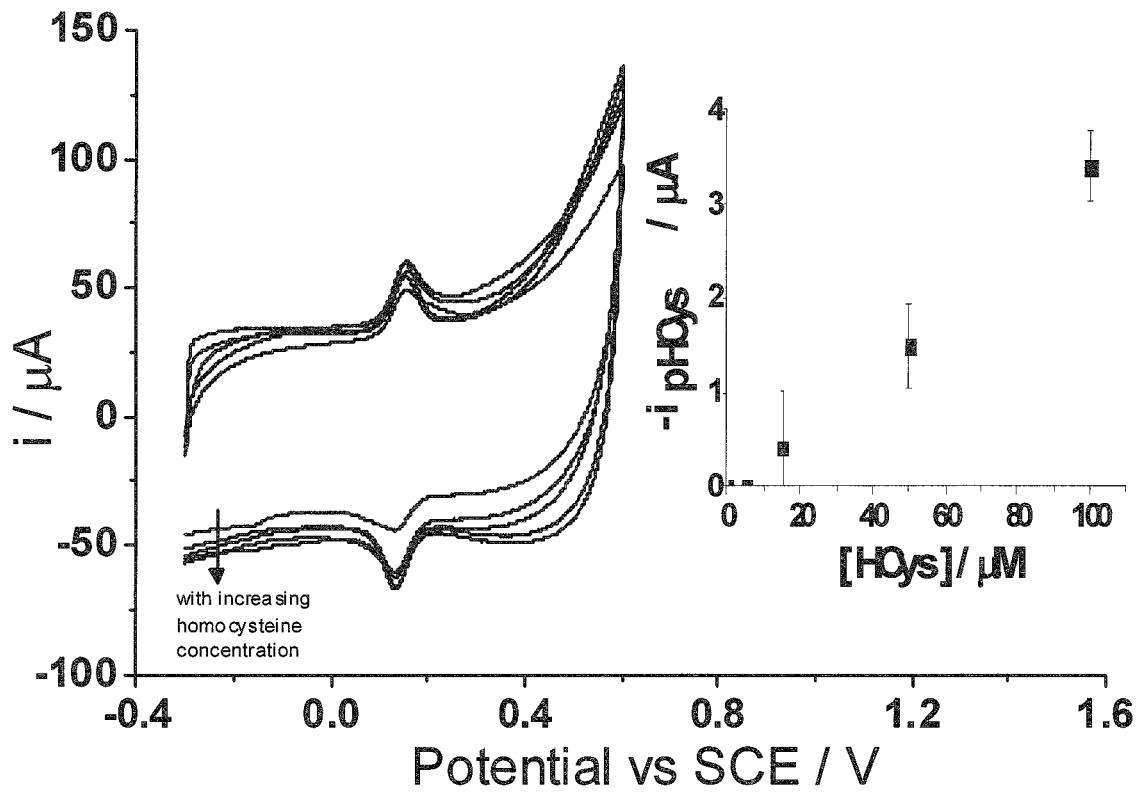
FIG. 14: Cyclic voltammogram (50 mVs$^{-1}$) of CAT-NC-GCE in PBS (pH 7.0 at 20° C.) with varying concentration of homocysteine. Inset: peak current of homocysteine product peak, $i_{p\ HCys}$, vs. homocysteine concentration.

FIG. 13 shows cyclic voltammograms (50 mVs$^{-1}$) of the electrochemical behaviour of the catechol (curve a) when 0.1 mM homocysteine is present in the solution (curve b). The figure illustrates that when homocysteine is added to the solution, an introduction of a new peak potential emerges (ca. −0.16 vs. SCE). This is due to the addition reaction of a thiol-containing molecule to the ortho-quinone mentioned earlier. Next, various concentration of homocysteine were added to PBS (pH 7.0), ranging from 0 to 0.1 mM (FIG. 14). The inset to the figure shows that the adduct peak (ca. −0.16 vs. SCE) increases linearly, $I(\mu A)=+0.033[HCys](\mu M)$, with homocysteine concentration.

Figure 15:
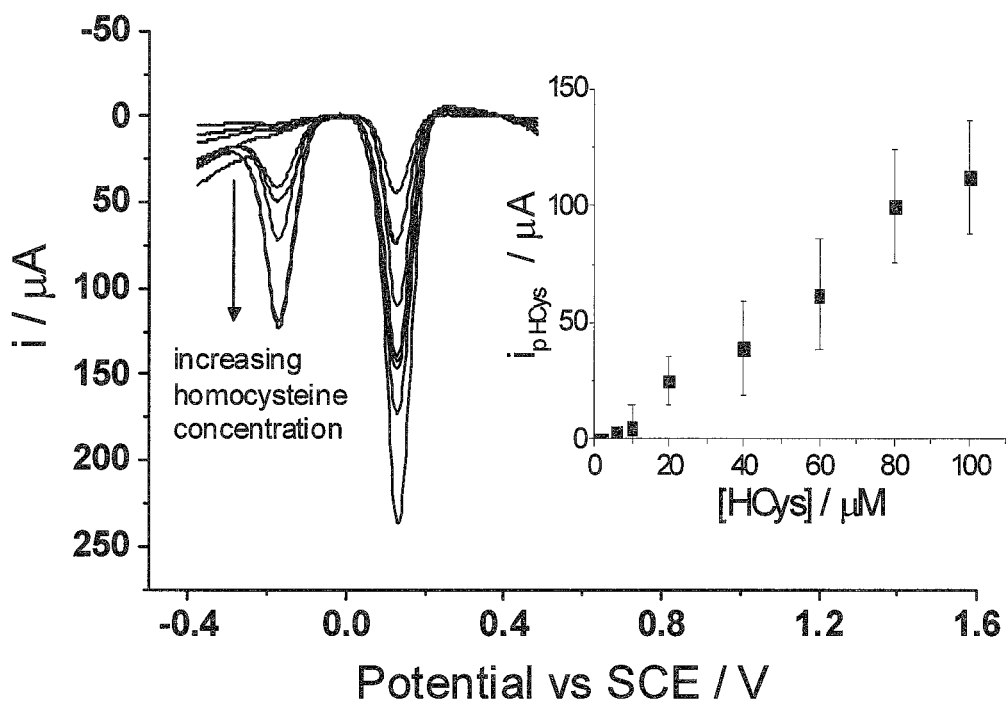
FIG. 15: Square wave voltammetry (freq. 25 Hz, amp. 50 mV, and step pot. 8.0 mV) response of CAT-NC-GCE with varying concentration of homocysteine, pH 7.0, ranging from 0-0.1 mM. Inset: Peak current at ca. −0.30 V (vs. SCE) plotted against concentration of homocysteine.

Square wave voltammetry was applied to increase the sensitivity towards homocysteine detection. The parameters were optimized at frequency 25 Hz, amplitude 50 mV and step potential 8.0 mV. FIG. 15 shows the product peak current of homocysteine (ca. −0.16 vs. SCE) increases with increasing homocysteine concentration. The inset to FIG. 15 indicates that there is a linear response, $I(\mu A)=+1.13[HCys](\mu M)$, when the current of the homocysteine product peak, $i_{p\ HCys}$, is plotted with homocysteine concentration. The limit of detection (LOD) was determined to be ca. 8.0 nM, using 3SD/S where SD is the standard deviation at zero analyte concentration and S is the sensitivity given by the gradient of the calibration curve. Using square wave voltammetry, the sensitivity of homocysteine detection, 1.13 µA µM$^{-1}$, was increased about thirty times compared to cyclic voltammetry.

Electrochemical Characterization of Cysteine (Cys)

Figure 16:
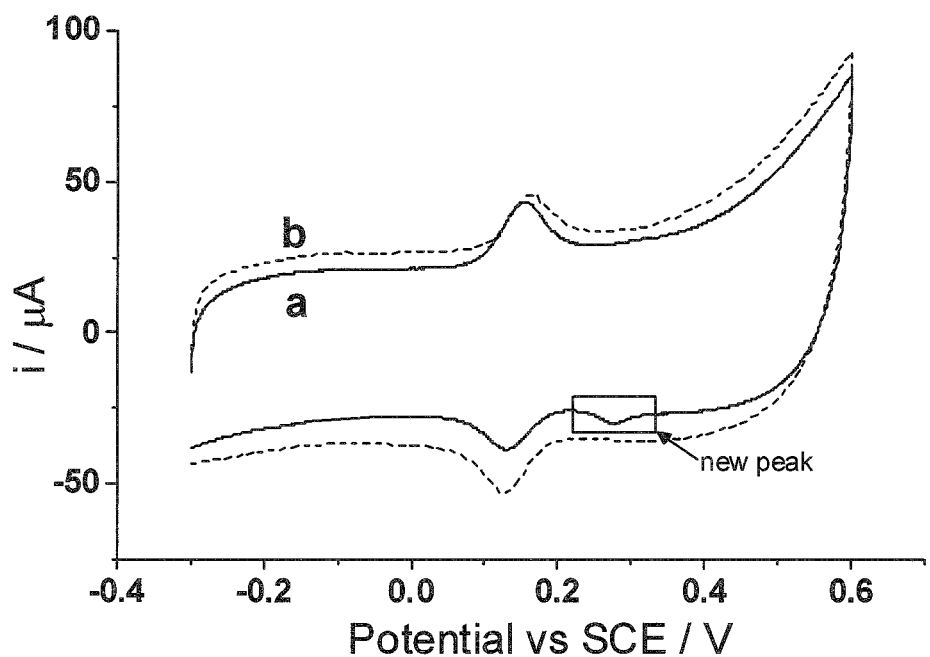
FIG. 16: Cyclic voltammogram (50 mV s$^{-1}$) of CAT-NC-GCE in a.) PBS (pH 7.0) (dotted) and b.) 0.1 mM cysteine (solid) (pH 7.0) at 20° C.
Figure 17:
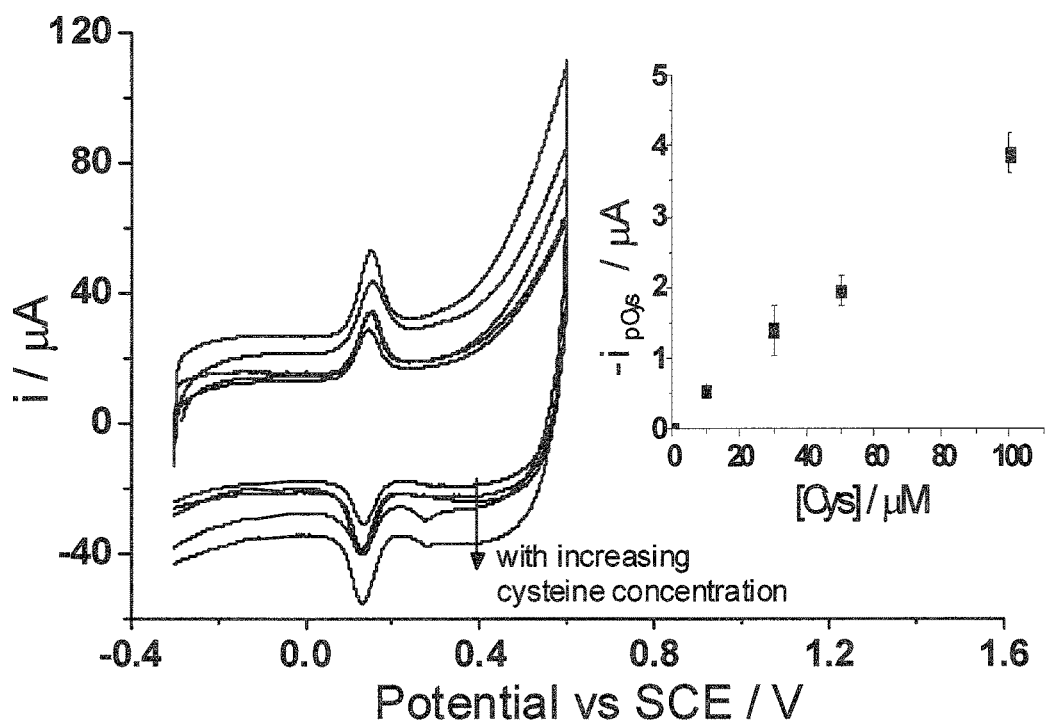
FIG. 17: Cyclic voltammogram (50 mVs$^{-1}$) of CAT-NC-GCE in PBS (pH 7.0) with varying concentration of cysteine. Inset: peak current of cysteine product peak, $i_{pCys}$, vs. cysteine concentration.

A solution containing 0.1 mM cysteine, Cys, (pH 7.0) was initially tested using cyclic voltammetry (50 mVs$^{-1}$) at the CAT-NC-GCE. FIG. 16, shows a result that a product peak appears ca. +0.30 V (vs. SCE). Cysteine, being a thiol-containing compound, can also react with catechol via 1,4-Michael addition reaction as in scheme (2). To see the influence of different cysteine concentrations, cyclic voltammetry (50 mVs$^{-1}$) was applied to different concentrations ranging, 0-0.1 mM (FIG. 17). The inset to FIG. 17 shows that the cysteine product peak (ca. +0.30 V vs. SCE) increases also linearly with cysteine concentration, $I(\mu A)=+3.96[Cys](nM)$.

Figure 18:
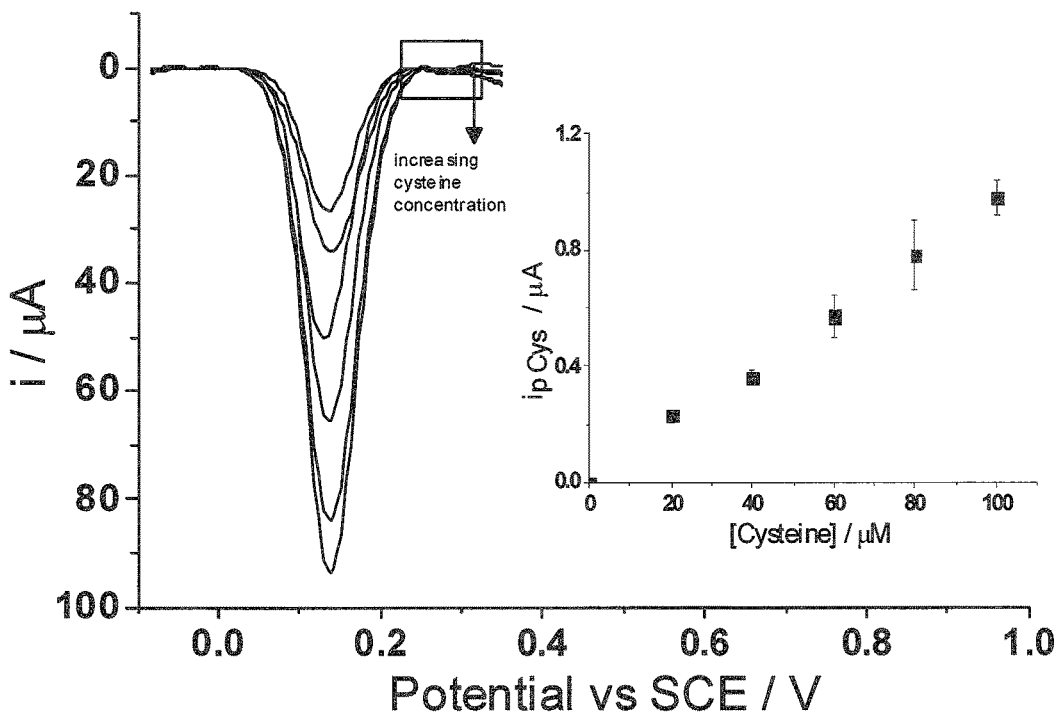
FIG. 18: Square wave voltammetry (freq. 25 Hz, amp. 50 mV, and step pot. 8.0 mV) response of CAT-NC-GCE with varying concentration of cysteine, pH 7.0, ranging from 0-0.1 mM. Inset: Peak current at ca. +0.30 V (vs. SCE) plotted against concentration of cysteine.

The same square wave voltammetry parameters as optimized during the homocysteine detection in this example (see above) were also applied to the electrochemical system of cysteine because the aim is to detect both homocysteine and cysteine in the same experiment. FIG. 18 shows the voltammogram of the CAT-NC-GCE at varying cysteine concentrations, 0-0.1 mM. The figure illustrates there is small product peak that emerges at ca. +0.28 V (vs. SCE) with increasing cysteine concentration; this is a result of the thiol containing molecule, cysteine, reacting with catechol (as described above). The inset to FIG. 18 further shows that there is a linear relationship, $I(\mu A)=+9.71[Cys](nM)$, when cysteine concentration is plotted with product peak current of cysteine, $i_{p\ Cys}$. The determined LOD is ca. 6.0 nM. However, sensitivity, 9.71 nM µA$^{-1}$, towards cysteine detection using square wave voltammetry is four times less.

Interference Studies

Figure 19:
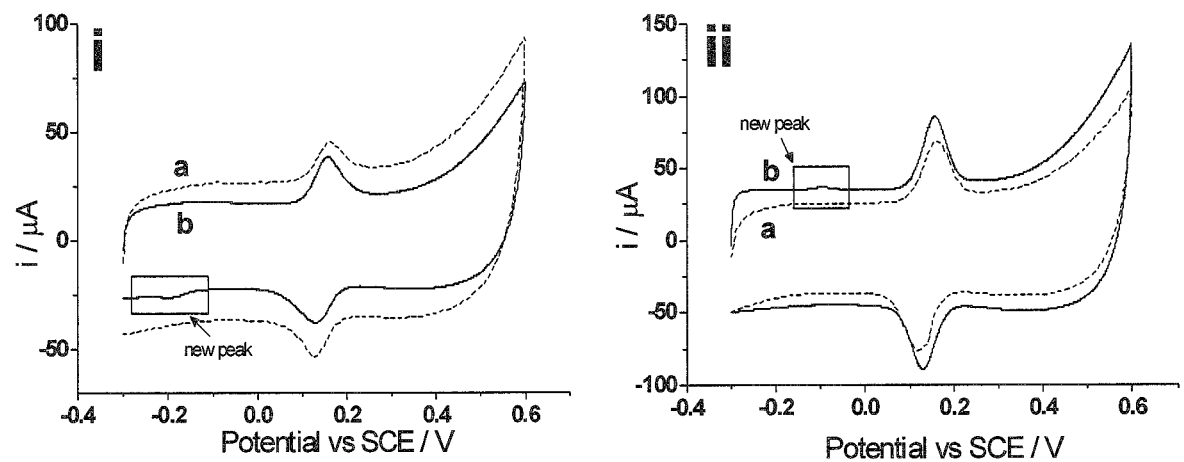
FIG. 19: Cyclic voltammograms (50 mVs$^{-1}$, pH 7.0) for CAT-NC-GCE in an absence a.) and presence b.) of 0.1 mM concentration of i.) glutathione ii.) ascorbic acid.

The selectivity of homocysteine and cysteine detection was investigated in PBS (pH 7.0) with the presence of other antioxidants, such as glutathione (GSH) and/or ascorbic acid (AA), as they can interfere by possibly interacting with the catechol. The interaction between catechol and the possible interfering analytes, GSH and AA, was investigated first. FIG. 19 shows the voltammograms of CAT-NC-GCE in PBS (pH7.0) (curve a) with the presence of 0.1 mM antioxidants (curve b): GSH (i), and AA (ii). In the presence of glutathione (FIG. 19i), there is an introduction of a new product peak ca. −0.20 V (vs. SCE). While in FIG. 11ii, the peak at ca. +0.30 V (vs. SCE) is due to the oxidation of AA at the electrode. Under inspection, GSH can interfere with the detection of HCys given that their peak positions are close to each other; thus making it difficult to quantify HCys in the presence of GSH.

Figure 20:
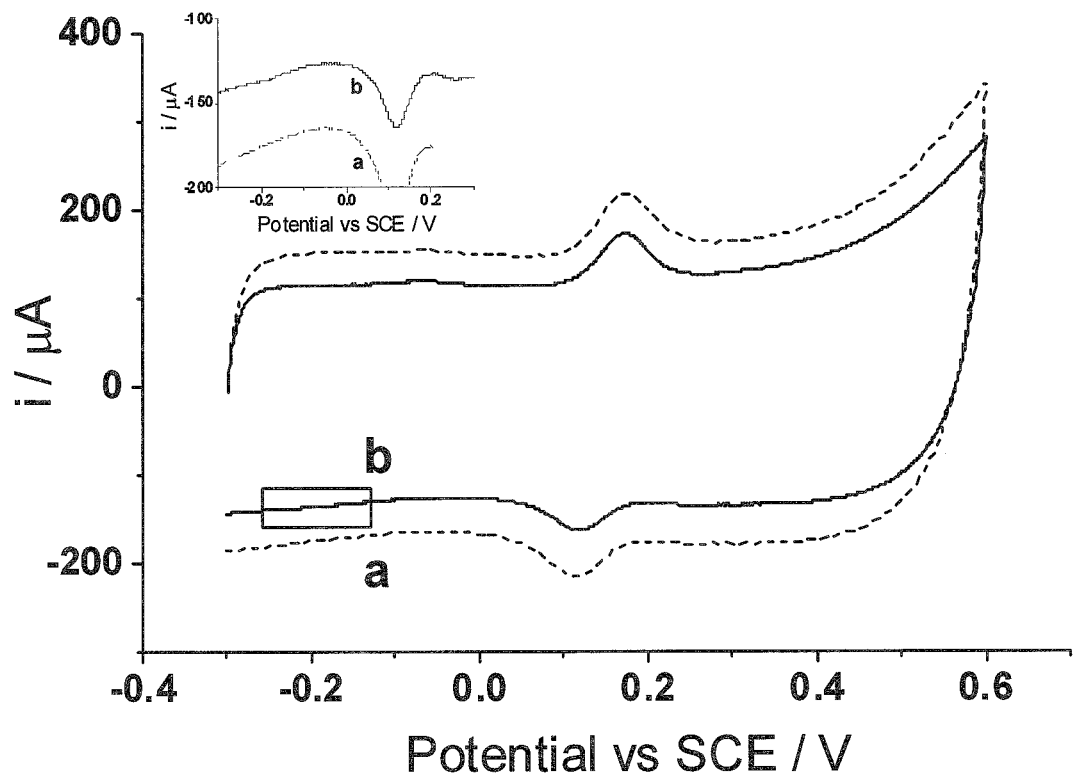
FIG. 20: Cyclic voltammetry (200 mVs$^{-1}$) of CAT-NC-GCE in a.) 0.1 mM GSH, Cys, and AA b.) 0.1 mM HCys, Cys, and AA (pH 7.0) at 20° C.

One method for homocysteine selectivity in the presence of glutathione is to take advantage of their reaction rates and molecular size by increasing the scan rate. The aim is to possibly outrun the catechol reaction with, the larger molecule, glutathione at a higher scan rate but be able to allow the catechol to react with homocysteine. In FIG. 20, an optimum faster scan rate of 200 mVs$^{-1}$ was applied to a solution containing a mixture of 0.1 mM Cys and AA with the presence of 0.1 mM GSH (curve a) and 0.1 mM HCys (curve b). There is no observable peak in the presence of glutathione when a higher scan rate is applied (curve a). When the same scan rate was applied to a solution containing homocysteine, there is slight indication of the homocysteine product peak (curve b). These voltammograms show that a peak at ca. −0.20 V (vs. SCE) at the higher scan rate corresponds to the reaction of homocysteine-catechol. Consequently, the cysteine product peak (ca. +0.30 V vs. SCE) current decreases significantly as a result of the higher scan rate. This value is consistently seen at the square wave voltammograms mentioned above (scan rate at 200 mVs$^{-1}$) for the cysteine-catechol product peak.

Figure 21:
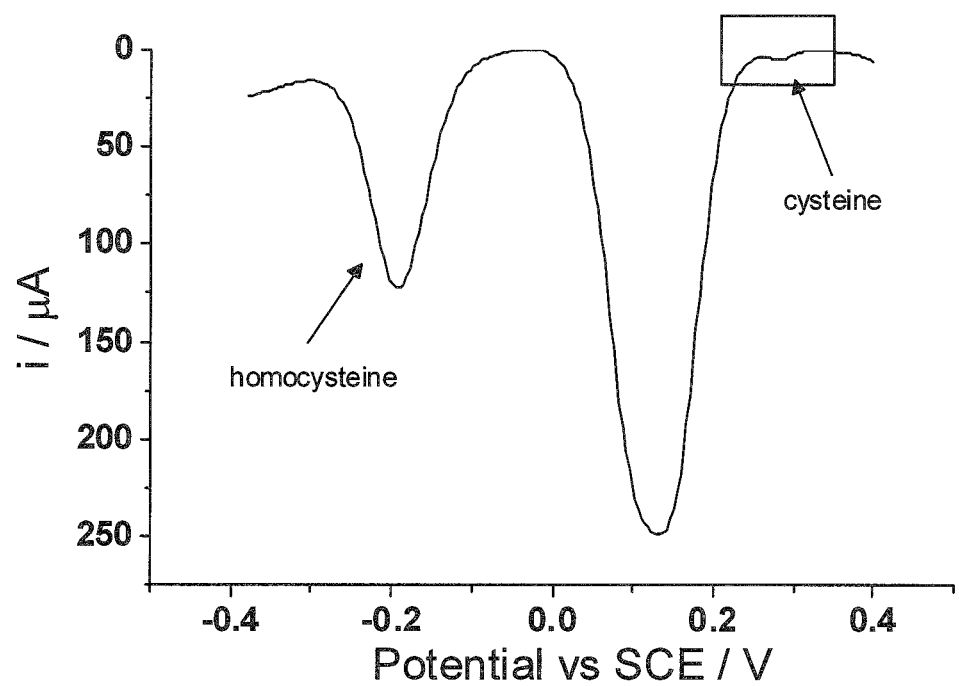
FIG. 21: Square wave voltammogram (200 mVs$^{-1}$) of CAT-NC-GCE in PBS solution (pH 7.0) with presence of homocysteine, cysteine, glutathione, and ascorbic acid. (freq. 25 Hz, amp. 50 mV, and step pot. 8.0 mV).

The same square wave parameters mentioned above were also applied to obtain simultaneous electrochemical detection of both homocysteine and cysteine in the presence of ascorbic acid and glutathione. Glutathione and ascorbic acid have been reported to be as high as 0.1 mM in biological samples and/or media, this concentration is considered to be the abnormal range for high risk for the diseases mentioned earlier. Therefore, testing at these high concentrations presents the likely worst-case scenario in a sample. FIG. 21 shows a reductive square wave voltammogram of a solution containing 0.1 mM of each of cysteine, homocysteine, glutathione, and ascorbic acid (pH 7.0) at the CAT-NC-GCE. The figure shows peaks with potentials at ca. +0.30 V, +0.10 V, and −0.20 V (vs. SCE) for cysteine product, catechol and homocysteine product respectively. The different peak potentials make it possible to detect both homocysteine and cysteine in the presence of all of the analytes mentioned above simultaneously.

Figure 22:
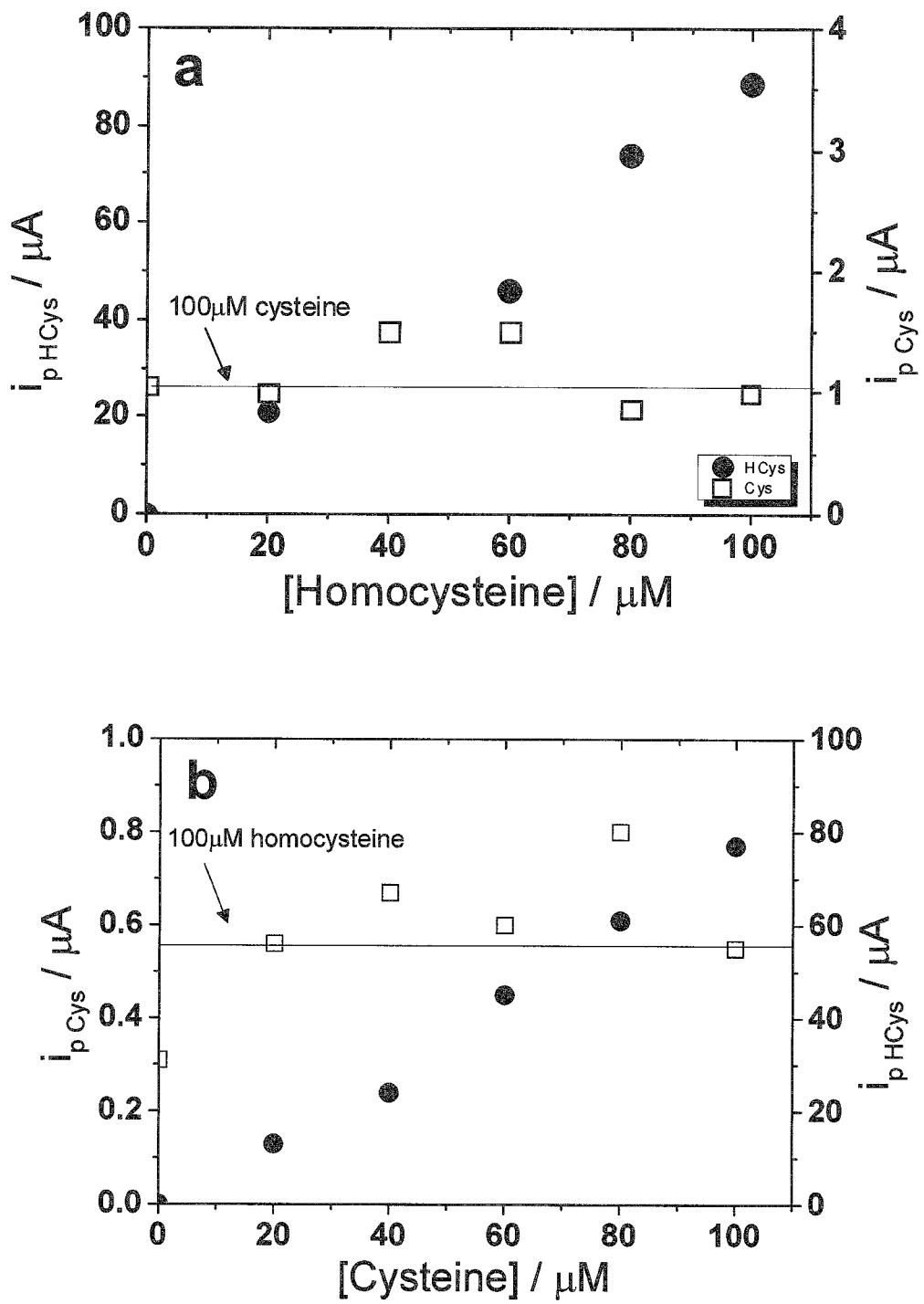
FIG. 22: Calibration plot of independent and simultaneous detection of a.) homocysteine and b.) cysteine in the presence of glutathione, and ascorbic acid PBS (pH 7.0) 20° C. at the CAT-NC-GCE.

An experiment was carried out in order to detect homocysteine and cysteine independently and simultaneously in the presence of both AA and GSH. A concentration of one analyte was held constant at 0.1 mM while the other varied, ranging from 0 to 0.1 mM. First, FIG. 22 shows a linear trend of peak current versus concentration of homocysteine (22a) and cysteine (22b) when in the presence of other analytes. The linear relationship of homocysteine with peak current in the presence of the other analytes is I ($\mu$A)=+0.88 [HCys]($\mu$M) with a determined LOD of 10 nM. Cysteine has a linear relationship at I ($\mu$A)=+7.50[Cys] (nM) with a LOD of ca. 6.0 $\mu$M. These values are similar to the sensitivity of pure homocysteine and cysteine. The horizontal line drawn across each plot indicates the median of the analyte that was held constant. The "error" of the analyte being held constant is due to limited reproducibility of the nanocarbon loading done to each electrode surface (minimum error, 30%) and not due to the detection method. Nonetheless, these values are comparative to these seen when GSH and AA are absent from the solution.

From Example 2 it can be concluded that catechol was successfully immobilized onto a nanocarbon modified glassy carbon electrode to facilitate the reaction of oxidized catechol with two thiol-containing molecules, homocysteine and cysteine. A simultaneous electrochemical detection of both homocysteine and cysteine was achieved separately first and then second in the presence of glutathione and ascorbic acid to determine their calibration curves. The sensitivity of homocysteine detection was (0.88±0.296) $\mu$A $\mu$M$^{-1}$ with a LOD of 10 nM and the sensitivity of cysteine detection was (7.50±0.20) $\mu$A nM$^{-1}$ with a LOD of 6.0 $\mu$M. These values are well within the concentration range of analytes, 0-0.1 mM, reported in biological samples. This demonstrates the possibility of having simultaneous quantitative detection of homocysteine and cysteine in the presence of glutathione and ascorbic acid.

Example 3: Detection of Total Antioxidant Concentrations of Glutathione, Cysteine, Homocysteine and Ascorbic Acid Using a Nanocarbon Paste Electrode In this example, the electrocatalytic reaction between catechol and the antioxidants, glutathione, cysteine, homocysteine and ascorbic acid is studied at a nanocarbon paste electrode and used to measure the total antioxidant concentration in aqueous solution. Two different approaches are described: one in which catechol is dissolved in solution and the second in which catechol is dissolved into the nanocarbon paste electrode. Similar limits of detection of 2.0 $\mu$M and 1.9 $\mu$M and sensitivities of 8.8×10$^{-3}$ $\mu$A/$\mu$M and 0.11 $\mu$M$^{-1}$ are reported, respectively at nanocarbon and nanocarbon-catechol paste electrodes. Three different commercial multivitamin drug samples were analysed and the results were in a good agreement with those from independent analysis.

Reagents

Catechol ($C_6H_6O_2$, Aldrich), L-cysteine ($C_3H_7NO_2S$, Sigma-Aldrich), DL-homocysteine ($C_4H_9NO_2S$, Sigma-Aldrich), glutathione ($C_{10}H_{17}N_3O_6S$, Sigma-Aldrich), ascorbic acid ($C_6H_8O_6$, Sigma-Aldrich), potassium phosphate dibasic ($K_2HPO_4$, Aldrich), potassium phosphate monobasic ($KH_2PO_4$, Sigma), nanocarbon particles (diameter 27±10 nm, Monarch 430®, Cabot Performance), mineral oil (Aldrich) were used as received without further purification. Phosphate buffer solution (PBS) was prepared using the adequate amount of $K_2HPO_4$ and $KH_2PO_4$ salts. All solutions were prepared using deionised water of resistivity not less than 18.2 M$\Omega$ cm at 25° C. (Millipore, Billerica, Mass., USA). Prior to experiments, all solutions were purged through nitrogen ($N_2$, BOC, Surrey) to remove oxygen from the system.

Apparatus

All electrochemical experiments were conducted at (25±1)° C. using an Autolab (Eco Chimie, Utrecht, The Netherlands), with a standard three-electrode configuration consisting of nanocarbon or nanocarbon-catechol paste as a working electrode, a graphite rod as a counter electrode and a saturated calomel electrode (SCE) as reference electrode. All experiments were performed at least three times.

Preparation of Nanocarbon and Nanocarbon-Catechol Paste Electrode

Nanocarbon:

The carbon paste was prepared by hand pasting nanocarbon with mineral oil (55:45) using a pestle and mortar. The pastes were kept at room temperature until used.

Nanocarbon-Catechol:

Catechol solution was prepared with a certain amount of solid catechol dissolved in acetone. Catechol is not soluble in mineral oil so the acetone is employed to initially dissolve it. The modified nanocarbon-catechol paste electrode was prepared by hand pasting nanocarbon with mineral oil and an aliquot of catechol solution using a pestle and mortar. The resulting paste was left for at least 30 mins in nitrogen atmosphere to evaporate the acetone. After the evaporation, solid catechol is assumed to be distributed within in the paste. The pastes were kept in nitrogen atmosphere at room temperature until used to avoid catechol oxidation.

For both pastes, unmodified and catechol-modified, the material was packed into the well of the working electrode to a depth of 1 mm. The surface exposed to the solution was polished using a weighing paper to give a smooth finish before use. The body of the working electrode was a Teflon tube tightly packed with the carbon paste. The electrical contact was provided by a copper wire.

Preparation of Samples

The antioxidants content of multivitamin drugs was determined by using the proposed method at unmodified and modified nanocarbon paste electrode. Five tables were weighed and triturated. The sample stock solutions were prepared by dissolving approximately 20 mg of powder in PBS in a 10 mL volumetric flask. Working solutions were prepared by the dilution of suitable volumes from the stock. Sample 1 contains ascorbic acid, cysteine and glutathione. Samples 2 and 3 contain ascorbic acid and glutathione.

Electrochemical Behaviour of Catechol in a Nanocarbon Paste Electrode

Figure 23:
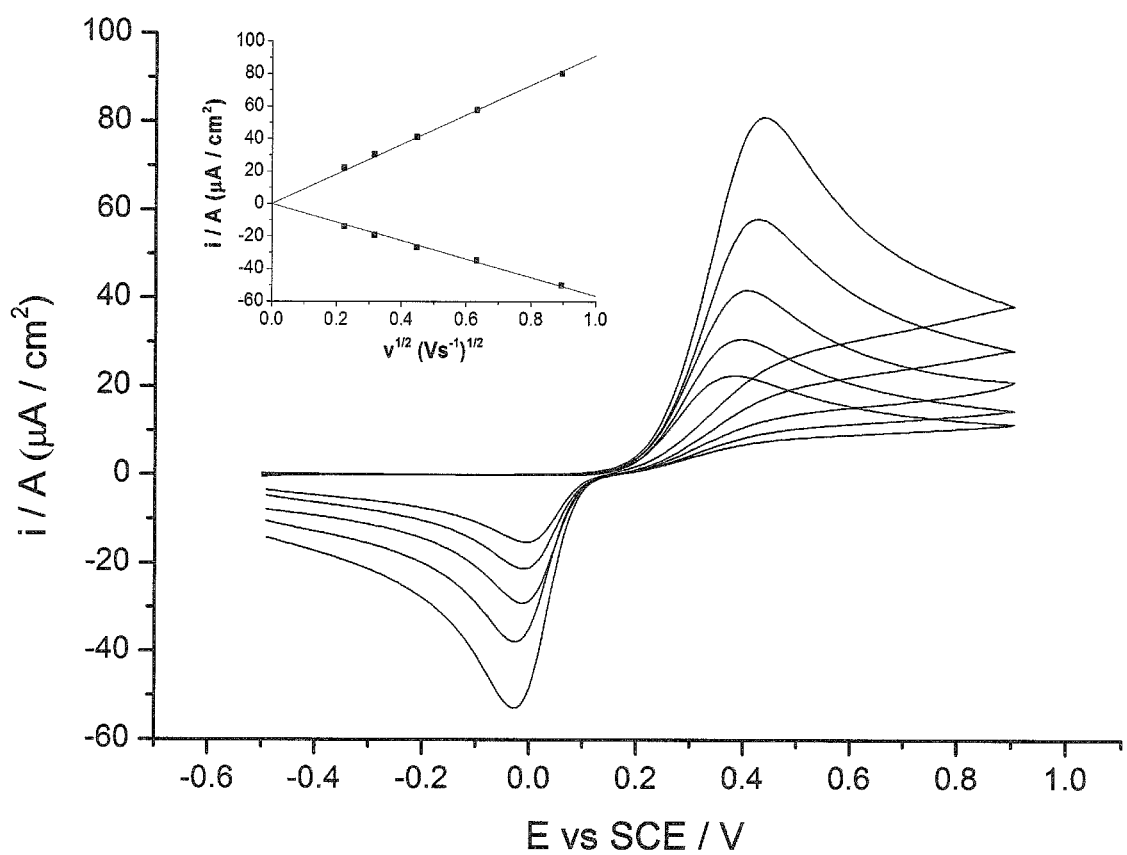
FIG. 23: Cyclic voltammetric responses for 100 μM catechol in PBS (pH=7.5) at different scan rate (from 50 to 800 mVs$^{-1}$) at nanocarbon electrode. Inset: plot of peak current against square root of scan rate. The current was normalized by electrode area. E°=+0.17V and D=7.0×10$^{-6}$ cm$^2$/s.

Initially, voltammetric studies at different scan rates (from 50 to 800 mVs$^{-1}$) involving the electrochemical behaviour of catechol in phosphate buffer solution (pH=7.5) using the nanocarbon paste electrode were performed (FIG. 23). The voltammograms show a chemically reversible redox process with a formal potential at ca +0.17 V (vs SCE). This process is attributed to the two electron oxidation of catechol to the corresponding o-quinone species in Scheme (3).

The inset in FIG. 23 shows the peak current increased linearly with the square root of scan rate, suggesting a diffusional process of catechol at this electrode. The catechol diffusion coefficient value was estimated as being $7.0 \times 10^{-6}$ cm$^2$/s.

Figure 1:
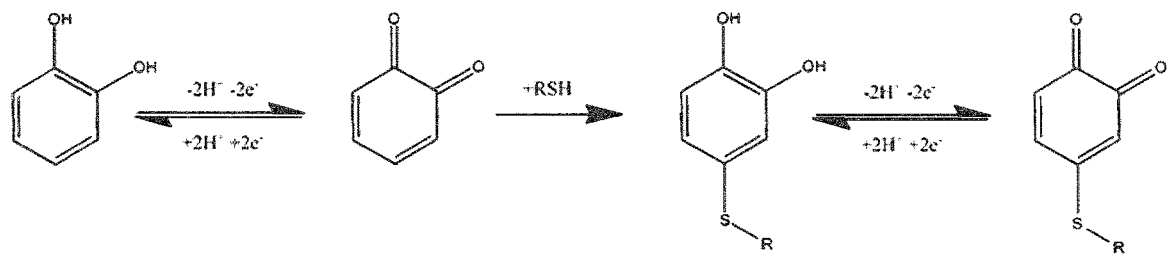
FIG. 1: Resulting voltammograms of a solution containing catechol ($I_{catechol}$) and thiol ($I_{catechol+thiol}$) via: (A) 1,4-Michael addition and (B) Electrocatalytical reaction.
Figure 1:
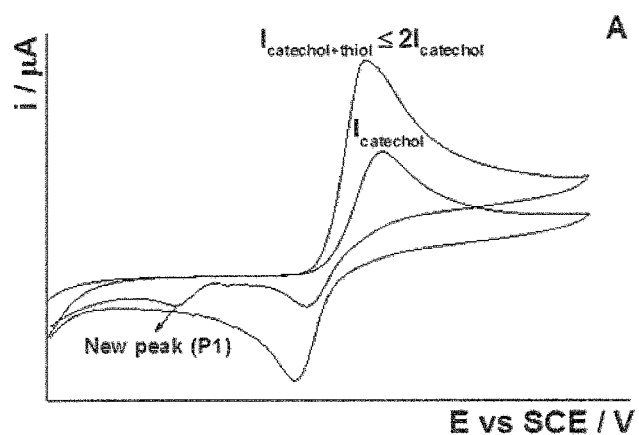
Figure 1:
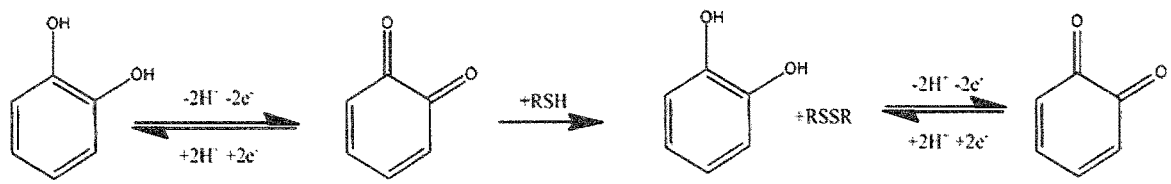
Figure 1:
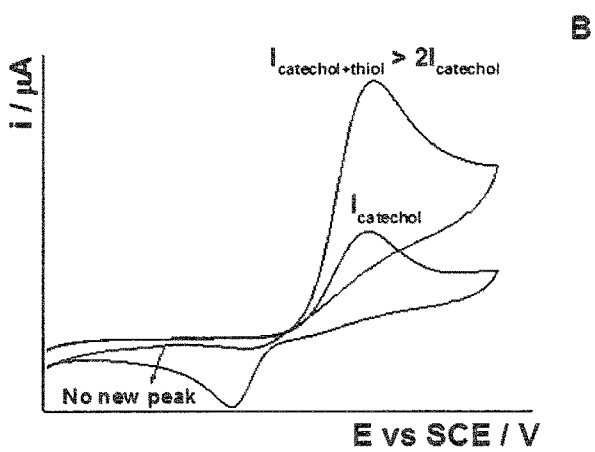
Figure 24:
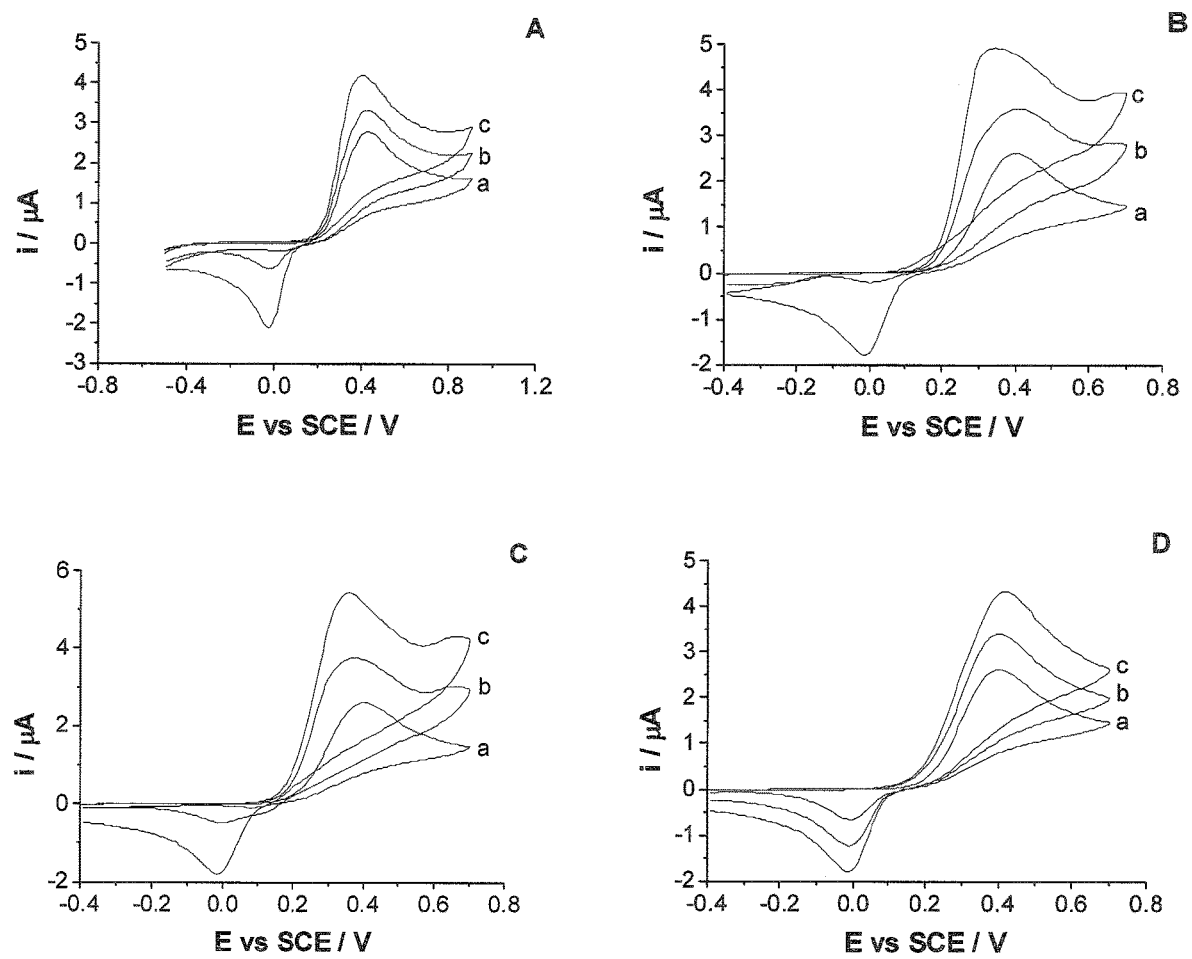
FIG. 24: Cyclic voltammetric responses for 100 μM catechol in PBS (pH=7.5) in the absence (a) and presence of glutathione (A), homocysteine (B), cysteine (C) and ascorbic acid (D) using nanocarbon paste electrode. Different concentrations were added (b) 40 and (c) 100 μM. v=100 mVs$^{-1}$.
Figure 25:
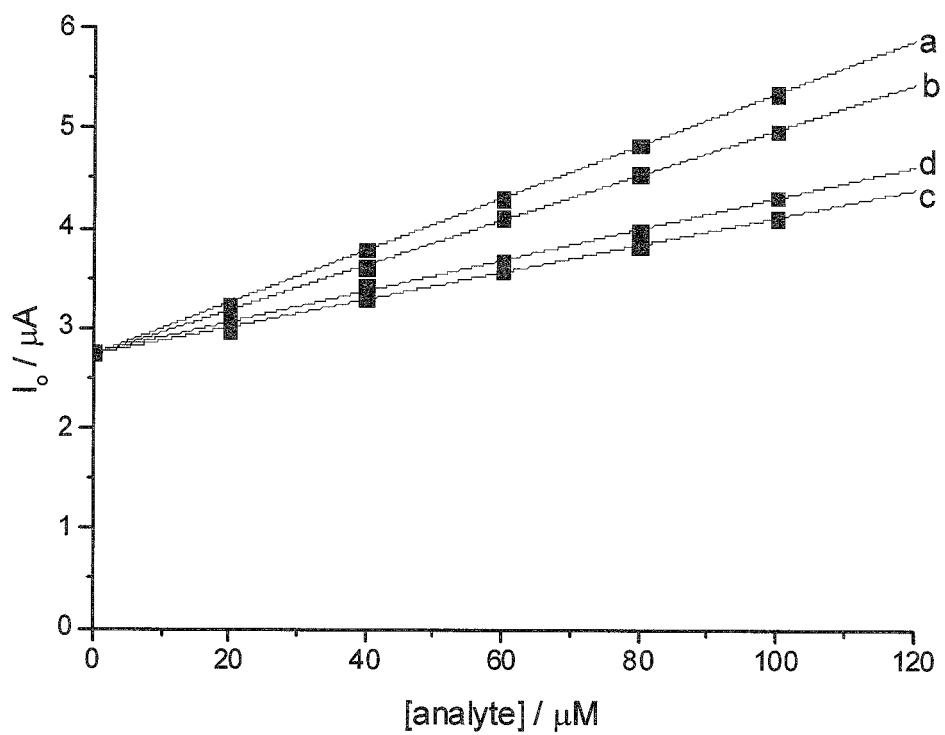
FIG. 25: Calibration curve for (a) cysteine, (b) homocysteine, (c) glutathione and (d) ascorbic acid using a nanocarbon paste electrode and catechol in solution. [Catechol]=100 μM.

Catechol in Solution—Detection of the Antioxidants Glutathione, Cysteine, Homocysteine and Ascorbic Acid The characterization of the reaction between the electrochemically generated o-quinone and the antioxidants, glutathione, cysteine, homocysteine and ascorbic acid, was carried out at a nanocarbon paste electrode using cyclic voltammetry (100 mVs$^{-1}$). The corresponding voltammetric responses of 100 µM catechol (pH=7.5) in the absence (curve a) and presence (curves b and c) is of glutathione (A), homocysteine (B), cysteine (C) and ascorbic acid (D) are detailed in FIG. 24. FIG. 24, curve a, shows the oxidation of catechol and the addition of antioxidants led to an increase in the height of the oxidation peak and a decrease in the magnitude of the reduction peak as shown in all the cases (curves b and c) indicating an electrocatalytic reaction (the same behaviour detailed at FIG. 1B) rather than 1,4-Michael addition (FIG. 1A). In all cases, an analytical curve was obtained by plotting oxidation peak current ($I_o$) versus concentration (FIG. 25). In some situations it was not possible to measure the reduction current peak, because at high concentration of the analytes, it decreases to zero. The sensitivity for cysteine is 0.026 µA/µM, for glutathione is 0.014 µA/µM, for homocysteine is 0.023 µA/µM and for ascorbic acid is 0.016 µA/µM. All these sensitivities were obtained in pure solution. The sensitivities differ a little from compound to compound. The data show that the system is more sensitive to cysteine than glutathione. Homocysteine and cysteine show similar sensitivity. The detection limits for each individual compound are: 1.7, 3.2, 2.0 and 2.8 µM, respectively, for cysteine, glutathione, homocysteine and ascorbic acid.

Figure 26:
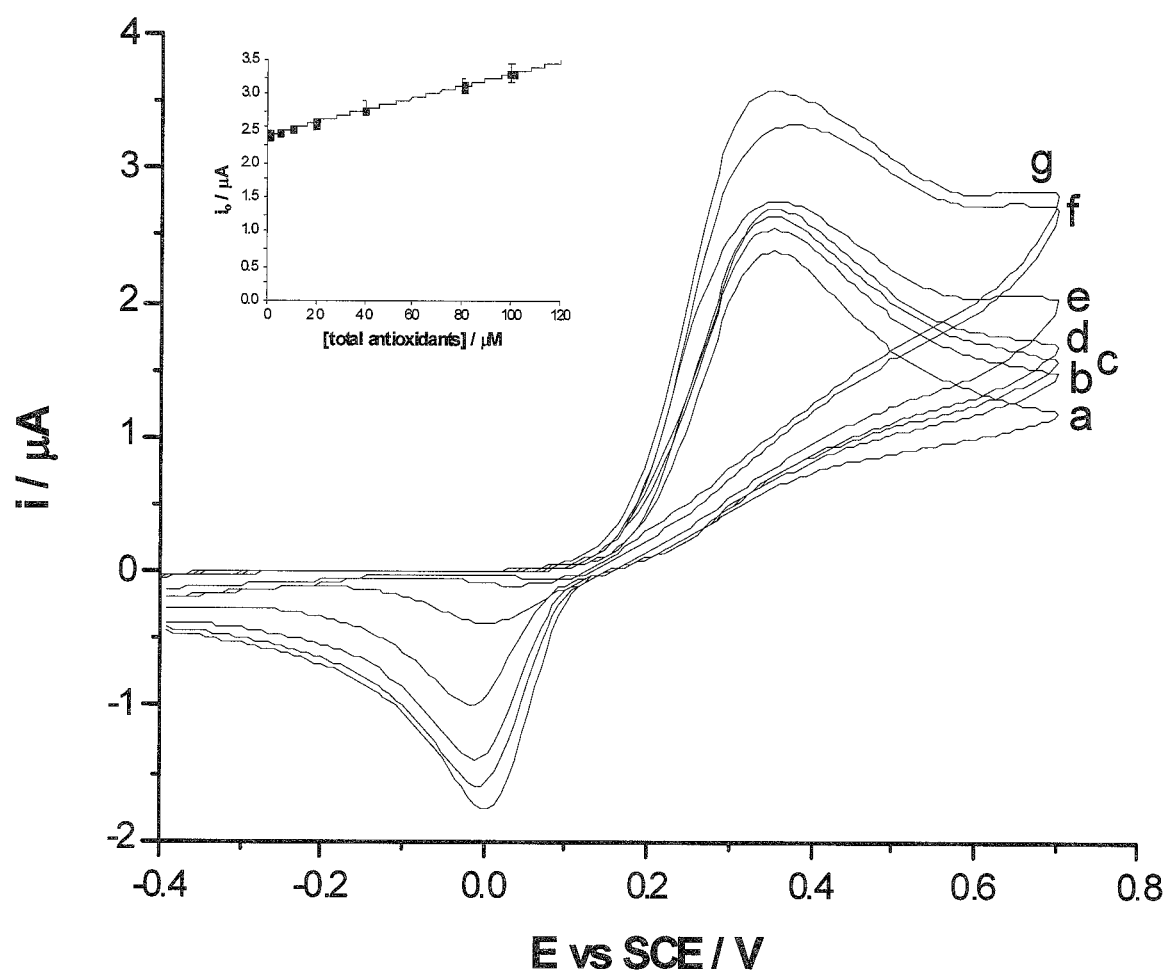
FIG. 26: Cyclic voltammetric responses for 100 μM catechol in PBS (pH=7.5) in the absence (a) and presence of total antioxidants at different concentrations (b) 5 μM, (c) 10

The nanocarbon paste electrode is not selective. All of the analytes showed similar responses. However, this observation enables a strategy for the detection of the total concentrations. Accordingly, cyclic voltammograms were carried out in mixtures of glutathione, homocysteine, cysteine and ascorbic acid. Different total concentrations were chosen from 5 to 100 µM. For each one, different mixtures were prepared as shown in Table 1. FIG. 26 shows the cyclic voltammograms response for different total antioxidants mixtures and the analytical curve (inset). The linear equation obtained was $I_o$ (µA)=2.409+0.0088[antioxidants] (µM). The reproducibility for each different total concentration was better than 5% (n=3) and the detection limit was 2.0 µM, demonstrating that the nanocarbon paste electrode is efficient for the detection of total antioxidant concentrations. These values reflect the analytical results for the range of composition studied in Table 1: 10%<[analyte]<40%, this in turn reflects the use in the medicine analysis reported below. Using the equation obtained for total antioxidants ($I_o$ (µA) =2.409+0.0088[antioxidants] (µM)) to calculate the concentration of 100% glutathione (100 µM–$I_o$=4.11) or 100% cysteine (100 µM–$I_o$=5.35), values of 193 µM and 334 µM are, respectively, obtained. Both values are over estimates because the sensitivities of pure individual molecules (cysteine 0.026 µA/µM, glutathione 0.014 µA/µM) and total antioxidants (0.0088 µA/µM) are not similar as each molecule contributes differently in the absence or presence of other compounds. However, in the application to biological samples or multivitamin drugs, the antioxidants are found mixed not isolated and analyses to within a certain tolerance are still valuable.

TABLE 1

Different mixtures and the oxidation current obtained from cyclic voltammetry using nanocarbon paste electrode.

| Mix | [Glutathione]/ µM | [Homocysteine]/ µM | [Cysteine]/ µM | [Ascorbic acid]/µM | [Total]/ µM | Io/µA |
|---|---|---|---|---|---|---|
| A | 25.0 | 25.0 | 25.0 | 25.0 | 100 | 3.41 |
| B | 25.0 | 25.0 | 35.0 | 15.0 | 100 | 3.29 |
| C | 25.0 | 25.0 | 15.0 | 35.0 | 100 | 3.16 |
| D | 25.0 | 35.0 | 15.0 | 25.0 | 100 | 3.32 |
| E | 25.0 | 15.0 | 35.0 | 25.0 | 100 | 3.10 |
| F | 35.0 | 15.0 | 25.0 | 25.0 | 100 | 3.28 |
| G | 15.0 | 35.0 | 25.0 | 25.0 | 100 | 3.39 |
| H | 15.0 | 25.0 | 25.0 | 35.0 | 100 | 3.49 |
| I | 35.0 | 25.0 | 25.0 | 15.0 | 100 | 3.32 |
| A | 20.0 | 20.0 | 20.0 | 20.0 | 80.0 | 2.88 |
| B | 20.0 | 20.0 | 30.0 | 10.0 | 80.0 | 3.04 |
| C | 20.0 | 20.0 | 10.0 | 30.0 | 80.0 | 3.12 |
| D | 20.0 | 30.0 | 10.0 | 20.0 | 80.0 | 3.17 |
| E | 20.0 | 10.0 | 30.0 | 20.0 | 80.0 | 3.14 |
| F | 30.0 | 10.0 | 20.0 | 20.0 | 80.0 | 3.13 |
| G | 10.0 | 30.0 | 20.0 | 20.0 | 80.0 | 3.19 |
| H | 10.0 | 20.0 | 20.0 | 30.0 | 80.0 | 3.05 |
| I | 30.0 | 20.0 | 20.0 | 10.0 | 80.0 | 3.26 |
| A | 10.0 | 10.0 | 10.0 | 10.0 | 40.0 | 2.66 |
| B | 10.0 | 10.0 | 15.0 | 5.00 | 40.0 | 3.04 |
| C | 10.0 | 10.0 | 5.00 | 15.0 | 40.0 | 2.76 |
| D | 10.0 | 15.0 | 5.00 | 10.0 | 40.0 | 2.73 |
| E | 10.0 | 5.00 | 15.0 | 10.0 | 40.0 | 2.83 |
| F | 15.0 | 5.00 | 10.0 | 10.0 | 40.0 | 2.71 |
| G | 5.00 | 15.0 | 10.0 | 10.0 | 40.0 | 2.72 |
| H | 5.00 | 10.0 | 10.0 | 15.0 | 40.0 | 2.76 |
| I | 15.0 | 10.0 | 10.0 | 5.00 | 40.0 | 2.71 |
| A | 5.00 | 5.00 | 5.00 | 5.00 | 20.0 | 2.64 |
| B | 5.00 | 5.00 | 7.50 | 2.50 | 20.0 | 2.57 |
| C | 5.00 | 5.00 | 2.50 | 7.50 | 20.0 | 2.57 |
| D | 5.00 | 7.50 | 2.50 | 5.00 | 20.0 | 2.55 |
| E | 5.00 | 2.50 | 7.50 | 5.00 | 20.0 | 2.58 |
| F | 7.50 | 2.50 | 5.00 | 5.00 | 20.0 | 2.52 |
| G | 2.50 | 7.50 | 5.00 | 5.00 | 20.0 | 2.56 |
| H | 2.50 | 5.00 | 5.00 | 7.50 | 20.0 | 2.65 |
| I | 7.50 | 5.00 | 5.00 | 2.50 | 20.0 | 2.61 |
| A | 2.50 | 2.50 | 2.50 | 2.50 | 10.0 | 2.50 |
| B | 2.50 | 2.50 | 3.75 | 1.25 | 10.0 | 2.49 |
| C | 2.50 | 2.50 | 1.25 | 3.75 | 10.0 | 2.50 |
| D | 2.50 | 3.75 | 1.25 | 2.50 | 10.0 | 2.45 |
| E | 2.50 | 1.25 | 3.75 | 2.50 | 10.0 | 2.46 |
| F | 3.75 | 1.25 | 2.50 | 2.50 | 10.0 | 2.54 |
| G | 1.25 | 3.75 | 2.50 | 2.50 | 10.0 | 2.55 |
| H | 1.25 | 2.50 | 2.50 | 3.75 | 10.0 | 2.51 |
| I | 3.75 | 2.50 | 2.50 | 1.25 | 10.0 | 2.42 |
| A | 1.25 | 1.25 | 1.25 | 1.25 | 5.00 | 2.41 |
| B | 1.25 | 1.25 | 2.00 | 0.500 | 5.00 | 2.46 |
| C | 1.25 | 1.25 | 0.500 | 2.00 | 5.00 | 2.47 |
| D | 1.25 | 2.00 | 0.500 | 1.25 | 5.00 | 2.42 |
| E | 1.25 | 0.500 | 2.00 | 1.25 | 5.00 | 2.52 |
| F | 2.00 | 0.500 | 1.25 | 1.25 | 5.00 | 2.45 |
| G | 0.500 | 2.00 | 1.25 | 1.25 | 5.00 | 2.45 |
| H | 0.500 | 1.25 | 1.25 | 2.00 | 5.00 | 2.40 |
| I | 2.00 | 1.25 | 1.25 | 0.500 | 5.00 | 2.41 |

Catechol in Nanocarbon Paste—Detection of the Antioxidants Glutathione, Cysteine, Homocysteine and Ascorbic Acid An alternative method is the use of catechol mixed with nanocarbon paste so as to create a reagentless sensor. In this case, the experiment requires only the presence of the target to provide a signal and after the paste is polished and washed free of analyte, the sensor is ready for reuse.

Different percentages of catechol dissolved in the paste (0.03, 0.05, 0.1, 0.3, 0.6 and 1%) were used to make the modified electrode. FIG. 27 shows cyclic voltammetric responses for 0.05 and 0.3% nanocarbon-catechol paste in PBS (pH=7.5) at 100 mVs$^{-1}$. In both cases, similar electrochemical behaviour to catechol in solution was observed. Three scans with the same paste are presented in FIG. 27, showing that the electrode surface area is not reproducible (standard deviation is about 53%); this is probably due to the low amount of catechol generating limited homogeneity in the paste. Because of this irreproducible signal from electrode to electrode the absolute height of the oxidation or reduction peak cannot be used (without standard additions). To solve this problem the ratio between the oxidation ($I_o$) and reduction ($I_r$) peak currents may be used. The standard deviation in this case was 3.8% (n=3).

Using pastes with percentages of catechol 0.03, 0.05 and 0.1%, the sensor can quantify less than 20 μM of antioxidants and using pastes with percentages of catechol 0.3, 0.6 and 1%, the electrode can detect up to 80 μM of antioxidants with different sensitivity. Nanocarbon pastes with high percentages of catechol lose sensitivity because low concentrations of antioxidants do not affect significantly the signal of catechol. For further studies, the modified electrode containing 0.3% of catechol was chosen because this electrode is more sensitive to the antioxidants and can detect a large range (up to 80 μM) of antioxidants.

Cyclic voltammograms were recorded at 100 mVs$^{-1}$, using the nanocarbon-catechol paste chosen before, in different concentrations of (a) cysteine, (b) homocysteine, (c) glutathione and (d) ascorbic acid separately in order to obtain individual analytical curves. The calibration curves (FIG. 28) shows a linear relationship for all individual antioxidants. The sensitivity for cysteine is 0.108 μM$^{-1}$, for glutathione is 0.076 μM$^{-1}$, for homocysteine is 0.088 μM$^{-1}$ and for ascorbic acid is 0.066 μM$^{-1}$. The data show that the nanocarbon-catechol paste electrode is more sensitive to cysteine, having a similar behaviour to the nanocarbon paste electrode. The detection limits for each individual analyte are: 1.9, 1.2, 2.7 and 2.3 μM, respectively, for cysteine, glutathione, homocysteine and ascorbic acid.

As the nanocarbon-catechol paste electrode is not totally selective, various analytes which might interfere with the measurement of the antioxidants (urea, uric acid, creatinine, glucose and hydrogen peroxide) were tested and the results are shown in Table 2. The data show that the ratios obtained for all the tested analytes (creatinine: 1.80, glucose: 1.91, hydrogen peroxide: 1.76, urea: 1.86 and uric acid: 1.89) are very similar to that obtained only in pure PBS (1.85±0.07), indicating that these analytes do not react significantly with the o-quinone.

TABLE 2

Ratio between $I_o$ and $I_r$ for different analytes

| Analytes | Concentration/μM | −Io/Ir |
|---|---|---|
| Creatinine | 100 | (1.80 ± 0.08) |
| Glucose | 100 | (1.91 ± 0.08) |
| Hydrogen peroxide | 100 | (1.76 ± 0.08) |
| Urea | 100 | (1.86 ± 0.08) |
| Uric acid | 100 | (1.89 ± 0.09) |

Nanocarbon-catechol paste in PBS: −$I_o$/$I_r$ = (1.85 ± 0.07)

To detect the total concentration of glutathione, cysteine, homocysteine and ascorbic acid, cyclic voltammograms were carried out in various mixtures of glutathione, homocysteine, cysteine and ascorbic acid. Different total concentrations (glutathione, homocysteine, cysteine and ascorbic acid) were chosen from 5 to 80 μM. For each one, different mixtures were prepared as shown in Table 3. FIG. 29 shows the cyclic voltammograms response for three mixtures for two different total concentrations. The data show that regardless of the combination of the different concentration, the ratio is almost the same (standard deviation <5%), indicating that in a mix the individual behaviour of each molecule does not significantly influence the amount output which is rather controlled by the total concentration of the species studies. FIG. 30 shows the calibration curve for the total concentration of antioxidants. The linear equation obtained was −Io/Ir (μA)=1.79+0.11[antioxidants] (μM). The reproducibility for each different total concentration was between 3-5% (n=3) and the detection limit was 1.93 μM, demonstrating the good performance of the modified electrode. Table 4 shows the final comparison between the two systems. Both paste electrodes were efficient to quantify total antioxidants based in a reaction with electrochemically generated o-quinone. The nanocarbon-catechol paste electrode has the advantage that is a reagentless sensor in comparison with nanocarbon paste electrode. Preferably, it should be kept in a nitrogen atmosphere to avoid catechol oxidation.

TABLE 3

Different mixtures and the ratio −$I_o$/$I_r$ obtained from cyclic voltammetry using nanocarbon-catechol paste electrode

| Mix | [Glutathione]/μM | [Homocysteine]/μM | [Cysteine]/μM | [Ascorbic acid]/μM | [Total]/μM | −Io/Ir |
|---|---|---|---|---|---|---|
| A | 20.0 | 20.0 | 20.0 | 20.0 | 80.0 | 10.71 |
| B | 20.0 | 20.0 | 30.0 | 10.0 | 80.0 | 10.65 |
| C | 20.0 | 20.0 | 10.0 | 30.0 | 80.0 | 10.53 |
| D | 20.0 | 30.0 | 10.0 | 20.0 | 80.0 | 10.43 |
| E | 20.0 | 10.0 | 30.0 | 20.0 | 80.0 | 10.86 |
| F | 30.0 | 10.0 | 20.0 | 20.0 | 80.0 | 10.86 |
| G | 10.0 | 30.0 | 20.0 | 20.0 | 80.0 | 10.67 |
| H | 10.0 | 20.0 | 20.0 | 30.0 | 80.0 | 10.49 |
| I | 30.0 | 20.0 | 20.0 | 10.0 | 80.0 | 10.30 |
| A | 10.0 | 10.0 | 10.0 | 10.0 | 40.0 | 6.53 |
| B | 10.0 | 10.0 | 15.0 | 5.00 | 40.0 | 6.19 |
| C | 10.0 | 10.0 | 5.00 | 15.0 | 40.0 | 6.16 |
| D | 10.0 | 15.0 | 5.00 | 10.0 | 40.0 | 6.33 |
| E | 10.0 | 5.00 | 15.0 | 10.0 | 40.0 | 6.16 |
| F | 15.0 | 5.00 | 10.0 | 10.0 | 40.0 | 6.36 |
| G | 5.00 | 15.0 | 10.0 | 10.0 | 40.0 | 6.20 |
| H | 5.00 | 10.0 | 10.0 | 15.0 | 40.0 | 5.85 |
| I | 15.0 | 10.0 | 10.0 | 5.00 | 40.0 | 6.12 |
| A | 5.00 | 5.00 | 5.00 | 5.00 | 20.0 | 3.99 |
| B | 5.00 | 5.00 | 7.50 | 2.50 | 20.0 | 3.77 |
| C | 5.00 | 5.00 | 2.50 | 7.50 | 20.0 | 3.81 |
| D | 5.00 | 7.50 | 2.50 | 5.00 | 20.0 | 3.76 |
| E | 5.00 | 2.50 | 7.50 | 5.00 | 20.0 | 4.06 |
| F | 7.50 | 2.50 | 5.00 | 5.00 | 20.0 | 3.89 |
| G | 2.50 | 7.50 | 5.00 | 5.00 | 20.0 | 3.65 |
| H | 2.50 | 5.00 | 5.00 | 7.50 | 20.0 | 3.87 |
| I | 7.50 | 5.00 | 5.00 | 2.50 | 20.0 | 3.72 |
| A | 2.50 | 2.50 | 2.50 | 2.50 | 10.0 | 2.88 |
| B | 2.50 | 2.50 | 3.75 | 1.25 | 10.0 | 2.95 |
| C | 2.50 | 2.50 | 1.25 | 3.75 | 10.0 | 2.81 |
| D | 2.50 | 3.75 | 1.25 | 2.50 | 10.0 | 2.96 |
| E | 2.50 | 1.25 | 3.75 | 2.50 | 10.0 | 2.88 |
| F | 3.75 | 1.25 | 2.50 | 2.50 | 10.0 | 2.76 |
| G | 1.25 | 3.75 | 2.50 | 2.50 | 10.0 | 2.88 |
| H | 1.25 | 2.50 | 2.50 | 3.75 | 10.0 | 2.95 |
| I | 3.75 | 2.50 | 2.50 | 1.25 | 10.0 | 2.76 |
| A | 1.25 | 1.25 | 1.25 | 1.25 | 5.00 | 2.10 |
| B | 1.25 | 1.25 | 2.00 | 0.500 | 5.00 | 2.09 |
| C | 1.25 | 1.25 | 0.500 | 2.00 | 5.00 | 2.14 |
| D | 1.25 | 2.00 | 0.500 | 1.25 | 5.00 | 2.30 |
| E | 1.25 | 0.500 | 2.00 | 1.25 | 5.00 | 2.37 |
| F | 2.00 | 0.500 | 1.25 | 1.25 | 5.00 | 2.36 |
| G | 0.500 | 2.00 | 1.25 | 1.25 | 5.00 | 2.18 |
| H | 0.500 | 1.25 | 1.25 | 2.00 | 5.00 | 2.24 |
| I | 2.00 | 1.25 | 1.25 | 0.500 | 5.00 | 2.13 |

TABLE 4

Comparison between the nanocarbon paste and nanocarbon-catechol paste electrodes for total antioxidants detection

| Parameters | Nanocarbon paste | Nanocarbon-catechol paste |
|---|---|---|
| Store | Room temperature | Room temperature in $N_2$ atmosphere |
| Catechol | In solution: 100 µM | In the paste: 0.3% |
| Total antioxidants - range | 5 to 100 µM | 5 to 80 µM |
| Sensitivity | $8.8 \times 10^{-3}$ µA/µM | 0.11 µM$^{-1}$ |
| Detection limit | 2.0 µM | 1.9 µM |

Antioxidant Determination in Multivitamin Drug Samples

After the detection of glutathione, cysteine, homocysteine and ascorbic acid using unmodified and modified nanocarbon paste electrode, both paste electrodes were used to determine total antioxidant concentrations in commercial multivitamin drug samples with different formulations. The results were obtained using both the above reported analytical curves: $I_o$ (µA)=2.409+0.0088[antioxidants] (µM) and $-I_o/I_r$ (µA)=1.79+0.11[antioxidants] (µM), respectively, for unmodified and modified nanocarbon paste electrodes. Table 5 reports the results obtained with both paste electrodes compared to those expected as reported on the product. The agreement between results shown in the table confirms the sensors (unmodified and modified) consist of a reliable methodology to determine antioxidants in samples comprising multivitamins.

TABLE 5

Antioxidants content in commercial multivitamin drug samples with different formulations

| Samples | AA/ mol* | GSH/ mol* | Cys/ mol* | Total/ mol* | Nanocarbon paste electrode/mol | Nanocarbon-catechol paste electrode/mol |
|---|---|---|---|---|---|---|
| 1 | $2.8 \times 10^{-3}$ | $6.5 \times 10^{-6}$ | $1.6 \times 10^{-4}$ | $3.0 \times 10^{-3}$ | $(3.3 \pm 0.1) \times 10^{-3}$ | $(3.21 \pm 0.08) \times 10^{-3}$ |
| 2 | $4.5 \times 10^{-4}$ | $3.2 \times 10^{-5}$ | — | $4.8 \times 10^{-4}$ | $(4.72 \pm 0.05) \times 10^{-4}$ | $(4.7 \pm 0.1) \times 10^{-4}$ |
| 3 | $5.1 \times 10^{-4}$ | $8.1 \times 10^{-6}$ | — | $5.2 \times 10^{-4}$ | $(5.1 \pm 0.2) \times 10^{-4}$ | $(5.05 \pm 0.05) \times 10^{-4}$ |

AA = ascorbic acid;
GSH = glutathione;
Cys = cysteine
*reported on the product

From Example 3 it can be concluded that the application of nanocarbon paste electrodes for detecting total concentrations of glutathione, homocysteine, cysteine and ascorbic acid based on the reaction with electrochemically generated o-quinone may be achieved. The use of nanocarbon paste electrodes was demonstrated by measurement of the concentration of total antioxidants in multivitamin drug samples and the reliability of the method.

Example 4: Electrochemical Detection of Both Homocysteine and Glutathione Using Carbon Nanotube Modified Carbon Electrode (CNT-GCE)

Experiments were done to investigate the detection of both homocysteine and glutathione using catechol solution at the carbon nanotube modified carbon electrode. Initial results showed that upon applying a low scan rate using cyclic voltammetry (50 mVs$^{-1}$) to a solution containing 0.1 mM catechol, glutathione and homocysteine, an adduct peak appears containing the catechol reaction with both glutathione and homocysteine thus making it more challenging for quantification when both are present in the solution. This is due to the reaction of catechol taking place with both glutathione and homocysteine at the electrode. Accordingly, the following two step procedure is proposed to address the problem of quantifying either homocysteine or glutathione in the presence of each other.

Homocysteine selectivity was investigated by examining the reaction rates of glutathione and homocysteine with catechol. A higher voltage scan rate was applied with the aim to 'outrun' the glutathione-catechol reaction but allow the homocysteine-catechol reaction to still take place. An optimized scan rate of 500 mVs$^{-1}$ was applied to cyclic voltammetry of a solution containing 0.1 mM each of catechol, glutathione and/or homocysteine (PBS, pH 7.0) using CNT-GCE. The results show that little to no product peak appears when the high scan rate is applied to a solution containing catechol and glutathione while an analytically useful adduct peak appears in the presence of catechol and homocysteine. This suggests that the higher scan rate was fast enough to preclude the catechol reaction with glutathione but still allow the reaction to take place with homocysteine thus allowing selective determination of homocysteine at the CNT-GCE. This measurement at high scan rate thus allows the measurement of homocysteine.

Though the selective determination of homocysteine is achievable at high scan rate, the further concept of glutathione detection with the same sample is also addressed. For a solution containing both homocysteine and glutathione, a high cyclic voltammetry scan rate of 500 mVs$^{-1}$ can be first applied and then after agitation of the solution, a low scan rate of 50 mVs$^{-1}$ can be applied afterwards with cyclic voltammetry being measured at both scan rates. The concentration of homocysteine present in solution is first determined using the peak current at high scan rate using the analytical curve at this scan rate, for example I (µA)= (0.0478±0.0113) [HCys](µM), and taking into account the size and shape of the electrode. The homocysteine concentration, was used to calculate the peak current at the lower scan rate using a different curve, for example, I (µA)= (0.0250±0.00077) [HCys](µM), taking into account the size and shape of the electrode. This value may be subtracted from the total adduct peak current at the low scan rate thus providing the current for glutathione-catechol reaction. The glutathione concentration can then be determined using another appropriate calibration curve at 50 mVs$^{-1}$, such as I (µA)=(0.0146±0.00030) [GSH](µM).

To provide a preliminary test of this proposed procedure, a number of solutions containing homocysteine and glutathione with 0.1 mM catechol (PBS, pH7.0) at 20° C. at the CNT-GCE were tested. The three examples of analytical curves relate to a GC electrode a radius of ca. 1.5 mm and catechol concentration of 0.1 mM. The results can be seen in the table below (table 6) showing that this procedure provides good agreement with what is present in solution, for concentrations of each homocysteine and glutathione up to 10 μM. The proposed method will work generally providing both glutathione and homocysteine are of much lower concentration then the added catechol.

TABLE 6

Preliminary determination of homocysteine and glutathione with 0.1 mM catechol (PBS, pH 7.0) at 20° C. using CNT-GCE

|  |  | Run 1 | | Run 2 (repeated run with different electrode) | |
|---|---|---|---|---|---|
| Mixture | | Calculated | Calculated | Calculated | Calculated |
| HCys (μM) | GSH (μM) | HCys @ 500 mVs$^{-1}$ (μM) | GSH @ 50 mVs$^{-1}$ (μM) | HCys @ 500 mVs$^{-1}$ (μM) | GSH @ 50 mVs$^{-1}$ (μM) |
| 10 | 10 | 9.3 | 11.6 | 11.4 | 13.2 |
| 5 | 10 | 4.2 | 11.0 | 5.8 | 12.7 |
| 10 | 5 | 9.6 | 4.9 | 9.8 | 4.8 |
| 10 | 3 | 10.5 | 3.2 | 9.2 | 4.8 |
| 3 | 10 | 3.0 | 9.2 | 2.6 | 11.9 |
| 1 | 10 | 1.2 | 10.3 | 1.1 | 8.6 |
| 10 | 1 | 10.3 | 1.2 | 9.7 | 2.6 |

$I_{x@y}$ = peak current for catechol in the presence of x at y (mVs$^{-1}$).
[HCys$_{500\ mVs-1}$] = homocysteine concentration at applied scan rate, 500 mVs$^{-1}$.

The summary of the procedures and calculations used in connection with Example 4 is set out below.
1. Run cyclic voltammetry of mixed solution at 500 mVs$^{-1}$. ($I_{Hcys@\ 500\ mVs-1}$)
2. Stir solution. Run cyclic voltammetry of mixed solution at 50 mVs$^{-1}$. ($I_{Hcys+GSH@\ 50\ mVs-1}$)
3. Determine [Hcys] using, $I_{Hcys@\ 500\ mVs-1}$ from step 1 with equation, I (μA)=(0.0478±0.0113) [HCyS$_{500\ mVs-1}$](μM).
4. Determine $I_{p\ Hcys}$ at 50 mVs$^{-1}$, $I_{Hcys@\ 50\ mVs-1}$, using I (μA)=(0.0250±0.00077) [HCys$_{500\ mVs-1}$](μM).
5. Subtract $I_{p\ Hcys@\ 50\ mVs-1}$ (step 4) from $I_{p\ Hcys\ +GSH@\ 50\ mVs-1}$ (step 2) to give ($I_{p\ GSH\ @50\ mVs-1}$).
6. Determine [GSH] from current obtained, $I_{p\ GSH\ @50\ mVs-1}$, at step 5 using I (μA)=(0.0146±0.00030) [GSH](μM).

The invention claimed is:
1. A method of detecting a material comprising a thiol group in a sample, the method comprising:
 a) providing a carbon electrode;
 b) contacting said electrode with said sample in the presence of an optionally substituted catechol;
 c) carrying out an electrochemical procedure to convert catechol to ortho-quinone and monitoring the conversion wherein said ortho-quinone reacts with the material comprising a thiol group to form an electrochemical reaction product,
  wherein the method comprises determining a concentration of homocysteine in the presence of at least one of, or any combination of, glutathione, cysteine and ascorbic acid;
  wherein the electrochemical procedure comprises a voltammetry technique to determine the presence of the electrochemical reaction product; and
  wherein the voltammetry technique comprises:
   (i) applying a first scan rate of about 200 mVs$^{-1}$ to about 1500 mVs$^{-1}$ to preclude significant signal for a product peak of the glutathione-catechol reaction, to selectively determine the concentration of homocysteine in the sample, and
   (ii) applying a second scan rate of about 50 mVs$^{-1}$ or less for the appearance of an adduct peak of the catechol reaction with both glutathione and homocysteine.

2. The method according to claim 1, wherein the electrochemical reaction product is the 1,4-Michael addition reaction product of the ortho-quinone and the material comprising a thiol group, wherein the electrochemical reaction product comprises a disulfide and the regeneration of catechol.

3. The method according to claim 1, wherein the electrochemical reaction product is the 1,4-Michael addition reaction product of the ortho-quinone and the material comprising a thiol group.

4. The method according to claim 1, wherein the electrochemical reaction product comprises a disulfide and the regeneration of catechol.

5. The method according to claim 1, wherein the method comprises determining the total concentration of homocysteine and cysteine, optionally in the presence of ascorbic acid and glutathione.

6. The method according to claim 5, wherein the total concentration of homocysteine and cysteine is determined simultaneously.

7. The method according to claim 1, wherein the method comprises determining the total concentration of glutathione, cysteine, homocysteine and ascorbic acid.

8. The method according to claim 1, wherein the method comprises determining the concentration of homocysteine and glutathione.

9. The method according to claim 1, wherein the method comprises determining the concentration of homocysteine and glutathione in the presence of cysteine and/or ascorbic acid.

10. The method according to claim 1, wherein the method comprises determining the concentrations individually of homocysteine and of glutathione in a sample.

11. The method according to claim 1, wherein the method comprises determining the concentrations individually of homocysteine and of glutathione in a sample, wherein said sample further comprises cysteine and/or ascorbic acid.

12. The method according to claim 1, wherein the voltammetry technique comprises a cyclic voltammetry technique and/or a square wave voltammetry technique.

13. The method according to claim 12, wherein the voltammetry technique consists of a square wave voltammetry technique.

14. The method according to claim 12, wherein the voltammetry technique consists of a cyclic voltammetry technique.

15. The method according to claim 1, wherein the electrode is selected from the group consisting of a glassy carbon electrode (GCE), a carbon nanotube modified glassy carbon electrode (CNT-GCE), a nanocarbon modified glassy carbon electrode (NC-GCE) and a nanocarbon paste electrode.

16. The method according to claim 1, wherein the first scan rate is about 500 mVs$^{1}$ to about 1500 mVs.

* * * * *